(12) United States Patent
Vargas et al.

(10) Patent No.: US 6,537,288 B2
(45) Date of Patent: Mar. 25, 2003

(54) IMPLANTABLE MEDICAL DEVICE SUCH AS AN ANASTOMOSIS DEVICE

(75) Inventors: Jaime Vargas, Palo Alto, CA (US); James T. Nielsen, San Francisco, CA (US); Michael Hendricksen, Menlo Park, CA (US); Brendan M. Donohoe, San Francisco, CA (US); Stephen Yencho, Menlo Park, CA (US); Bernard Hausen, Menlo Park, CA (US)

(73) Assignee: Cardica, Inc., Menlo Park, CA (US)

( * ) Notice: Subject to any disclaimer, the term of this patent is extended or adjusted under 35 U.S.C. 154(b) by 21 days.

(21) Appl. No.: 10/003,406

(22) Filed: Dec. 6, 2001

(65) Prior Publication Data

US 2002/0042622 A1 Apr. 11, 2002

Related U.S. Application Data

(63) Continuation of application No. 09/437,428, filed on Nov. 15, 1999, which is a continuation-in-part of application No. 09/314,278, filed on May 18, 1999.

(51) Int. Cl.[7] .............................................. A61B 17/04
(52) U.S. Cl. ....................................................... 606/153
(58) Field of Search .............................. 606/152–155, 606/158, 108

(56) References Cited

U.S. PATENT DOCUMENTS

| 2,370,776 A | 3/1945 | Carlson ...................... 606/153 |
| 3,254,650 A | 6/1966 | Collito |
| 3,254,651 A | 6/1966 | Collito ........................ 606/153 |
| 3,519,187 A | 7/1970 | Kapitanov et al. |
| 3,774,615 A | 11/1973 | Lim et al. |
| 4,118,806 A | 10/1978 | Porier et al. |
| 4,214,587 A | 7/1980 | Sakura, Jr. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |

(List continued on next page.)

FOREIGN PATENT DOCUMENTS

| DE | 29713335 | 11/1997 |
| DE | 19732234 | 1/1999 |
| EP | 0 701 800 | 3/1996 |
| EP | 0 517 252 | 12/1996 |
| EP | 0 885 595 | 12/1998 |
| EP | 0 820 724 | 1/2000 |
| EP | 0 820 725 | 1/2000 |
| EP | 0 913 125 | 7/2000 |
| EP | 0 938 870 | 9/2000 |
| EP | 0 990 420 | 12/2000 |
| FR | 2316910 | 2/1977 |
| WO | 92/08513 | 5/1992 |
| WO | 96/25886 | 8/1996 |
| WO | 97/25002 | 7/1997 |
| WO | 97/27898 | 8/1997 |

(List continued on next page.)

*Primary Examiner*—Gary Jackson
(74) *Attorney, Agent, or Firm*—Brian A. Schar

(57) ABSTRACT

A medical device which can be implanted at a target site in a living body. The device includes an inner flange formed by radial expansion of the device and an outer flange formed by axial compression of the device. The device can include an implant portion and a discard portion which separate from each other during formation of the outer flange. The separation can occur by fracturing a frangible linkage or by mechanically separating a portion of the outer flange from a deployment tool. The device can be a one piece anastomosis device for connecting a graft vessel to a target vessel without the use of conventional sutures. The inner and outer flanges capture the edges of an opening in a target vessel and secure the graft vessel to the opening in the target vessel. The device greatly increases the speed with which anastomosis can be performed over known suturing methods.

28 Claims, 21 Drawing Sheets

U.S. PATENT DOCUMENTS

| | | |
|---|---|---|
| 4,503,568 A | 3/1985 | Madras |
| 4,523,592 A | 6/1985 | Daniel |
| 4,534,761 A | 8/1985 | Raible |
| 4,553,542 A | 11/1985 | Schenck et al. |
| 4,577,631 A | 3/1986 | Kreamer |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Schenck et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,773,420 A | 9/1988 | Green |
| 4,861,330 A | 8/1989 | Voss |
| 4,875,815 A | 10/1989 | Phillips, II |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Ramos Martinez |
| 5,187,796 A | 2/1993 | Wang et al. |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,326,205 A | 7/1994 | Anspach, Jr. et al. |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,401,131 A | 3/1995 | Yoshino |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | Lemole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,167,889 B1 | 1/2000 | Benetti |
| 6,022,367 A | 2/2000 | Sherts |
| 6,024,748 A | 2/2000 | Manzo et al. |

| | | | | | |
|---|---|---|---|---|---|
| 6,030,370 A | 2/2000 | Kupka et al. | WO | 98/40036 | 9/1998 |
| 6,030,395 A | 2/2000 | Nash et al. | WO | 98/42262 | 10/1998 |
| 6,036,699 A | 3/2000 | Andreas et al. | WO | 98/47430 | 10/1998 |
| 6,036,700 A | 3/2000 | Stefanchik et al. | WO | 98/55027 | 12/1998 |
| 6,036,702 A | 3/2000 | Bachinski et al. | WO | 99/08603 | 2/1999 |
| 6,036,703 A | 3/2000 | Evans et al. | WO | 99/11178 | 3/1999 |
| 6,036,704 A | 3/2000 | Yoon | WO | 99/17665 | 4/1999 |
| 6,036,705 A | 3/2000 | Nash et al. | WO | 99/18887 | 4/1999 |
| 6,050,472 A | 4/2000 | Shibata | WO | 99/21491 | 5/1999 |
| 6,053,390 A | 4/2000 | Green et al. | WO | 99/37218 | 7/1999 |
| 6,056,762 A | 5/2000 | Nash et al. | WO | 99/38441 | 8/1999 |
| 6,066,144 A | 5/2000 | Wolf et al. | WO | 99/38454 | 8/1999 |
| 6,066,148 A | 5/2000 | Rygaard | WO | 99/40851 | 8/1999 |
| 6,068,637 A | 5/2000 | Popov et al. | WO | 99/40868 | 8/1999 |
| 6,074,416 A | 6/2000 | Berg et al. | WO | 99/45848 | 9/1999 |
| 6,080,167 A | 6/2000 | Lyell | WO | 99/52481 | 10/1999 |
| 6,080,173 A | 6/2000 | Williamson, IV et al. | WO | 99/62406 | 12/1999 |
| 6,083,234 A | 7/2000 | Nicholas et al. | WO | 99/62409 | 12/1999 |
| 6,110,188 A | 8/2000 | Narciso, Jr. | WO | 99/62415 | 12/1999 |
| 6,113,612 A | 9/2000 | Swanson et al. | WO | 99/63910 | 12/1999 |
| 6,117,148 A | 9/2000 | Ravo et al. | WO | 99/65409 | 12/1999 |
| 6,120,432 A | 9/2000 | Sullivan et al. | WO | 00/09040 | 2/2000 |
| 6,146,393 A | 11/2000 | Wakabayashi | WO | 00/10486 | 3/2000 |
| 6,149,681 A | 11/2000 | Houser et al. | WO | 00/12013 | 3/2000 |
| 6,152,937 A | 11/2000 | Peterson et al. | WO | 00/15144 | 3/2000 |
| 6,152,945 A | 11/2000 | Bachinski et al. | WO | 00/15146 | 3/2000 |
| 6,165,185 A | 12/2000 | Shennib et al. | WO | 00/15147 | 3/2000 |
| 6,171,319 B1 | 1/2001 | Nobles et al. | WO | 00/15148 | 3/2000 |
| 6,171,321 B1 | 1/2001 | Gifford, III et al. | WO | 00/15149 | 3/2000 |
| 6,176,413 B1 | 1/2001 | Heck et al. | WO | 00/27310 | 5/2000 |
| 6,176,864 B1 | 1/2001 | Chapman | WO | 00/27311 | 5/2000 |
| 6,186,942 B1 | 2/2001 | Sullivan et al. | WO | 00/27312 | 5/2000 |
| 6,187,019 B1 | 2/2001 | Stefanchik et al. | WO | 00/27313 | 5/2000 |
| 6,187,020 B1 | 2/2001 | Zegdi et al. | WO | 00/33745 | 6/2000 |
| 6,190,396 B1 | 2/2001 | Whitin et al. | WO | 00/41633 | 7/2000 |
| 6,190,397 B1 | 2/2001 | Spence et al. | WO | 00/53104 | 9/2000 |
| 6,190,590 B1 | 2/2001 | Randall et al. | WO | 00/56223 | 9/2000 |
| 6,193,129 B1 | 2/2001 | Bittner et al. | WO | 00/56226 | 9/2000 |
| 6,193,734 B1 | 2/2001 | Bolduc et al. | WO | 00/56227 | 9/2000 |
| 6,206,912 B1 | 3/2001 | Goldsteen et al. | WO | 00/56228 | 9/2000 |
| 6,206,913 B1 | 3/2001 | Yencho et al. | WO | 00/59380 | 10/2000 |
| 6,235,054 B1 | 5/2001 | Berg et al. | WO | 00/66007 | 11/2000 |

FOREIGN PATENT DOCUMENTS

| | | | | | |
|---|---|---|---|---|---|
| WO | 97/31575 | 9/1997 | WO | 00/66009 | 11/2000 |
| WO | 97/47261 | 12/1997 | WO | 00/69343 | 11/2000 |
| WO | 98/07399 | 2/1998 | WO | 00/69346 | 11/2000 |
| WO | 98/19608 | 5/1998 | WO | 00/69349 | 11/2000 |
| WO | 98/19618 | 5/1998 | WO | 00/69364 | 11/2000 |
| WO | 98/19625 | 5/1998 | WO | 00/72764 | 12/2000 |
| WO | 98/19629 | 5/1998 | WO | 00/74579 | 12/2000 |
| WO | 98/19630 | 5/1998 | WO | 00/76405 | 12/2000 |
| WO | 98/19631 | 5/1998 | WO | 01/08601 | 2/2001 |
| WO | 98/19632 | 5/1998 | WO | 01/12074 | 2/2001 |
| WO | 98/19634 | 5/1998 | WO | 01/15607 | 3/2001 |
| WO | 98/19636 | 5/1998 | WO | 01/17440 | 3/2001 |
| WO | 98/30153 | 7/1998 | WO | 01/19257 | 3/2001 |
| WO | 98/3/7814 | 9/1998 | WO | 01/19259 | 3/2001 |
| | | | WO | 01/19284 | 3/2001 |
| | | | WO | 01/34037 | 5/2001 |

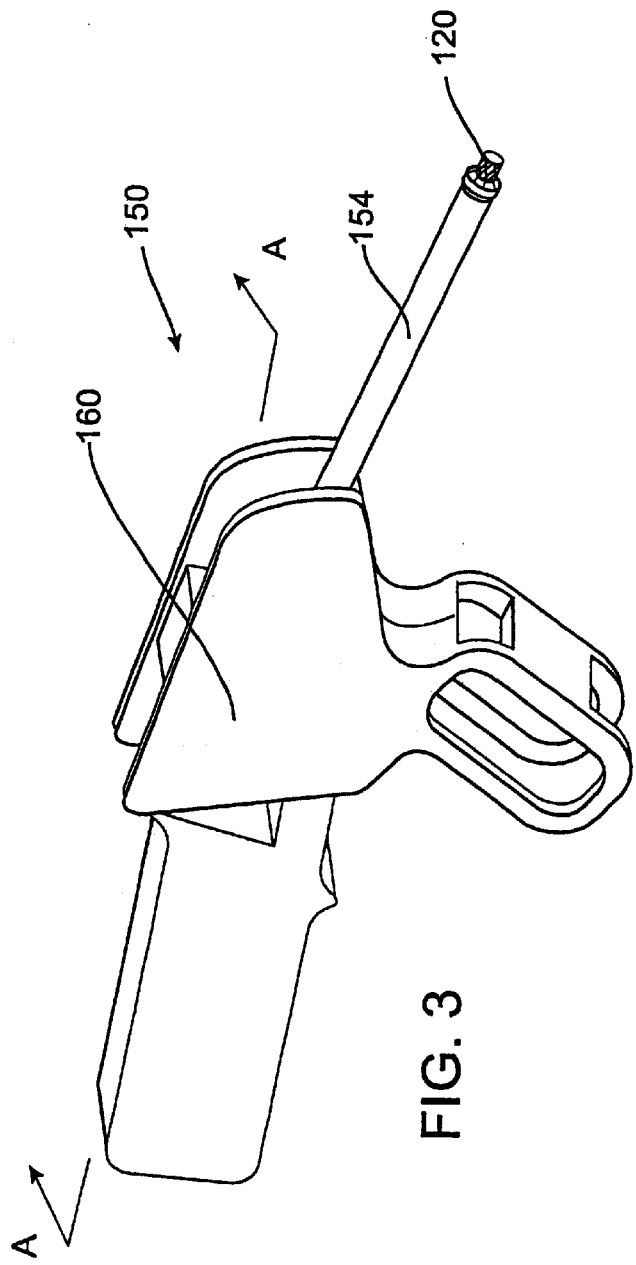
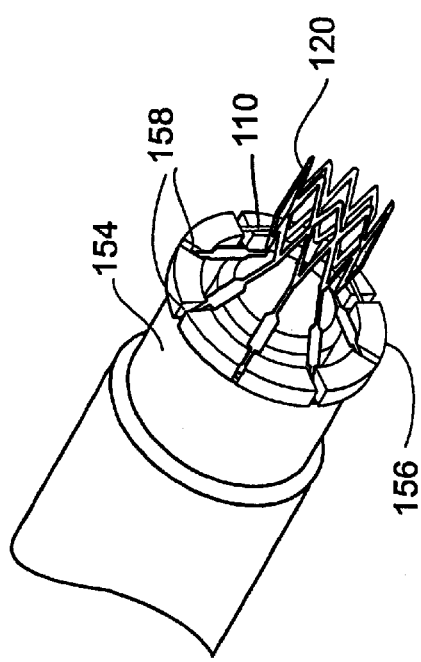

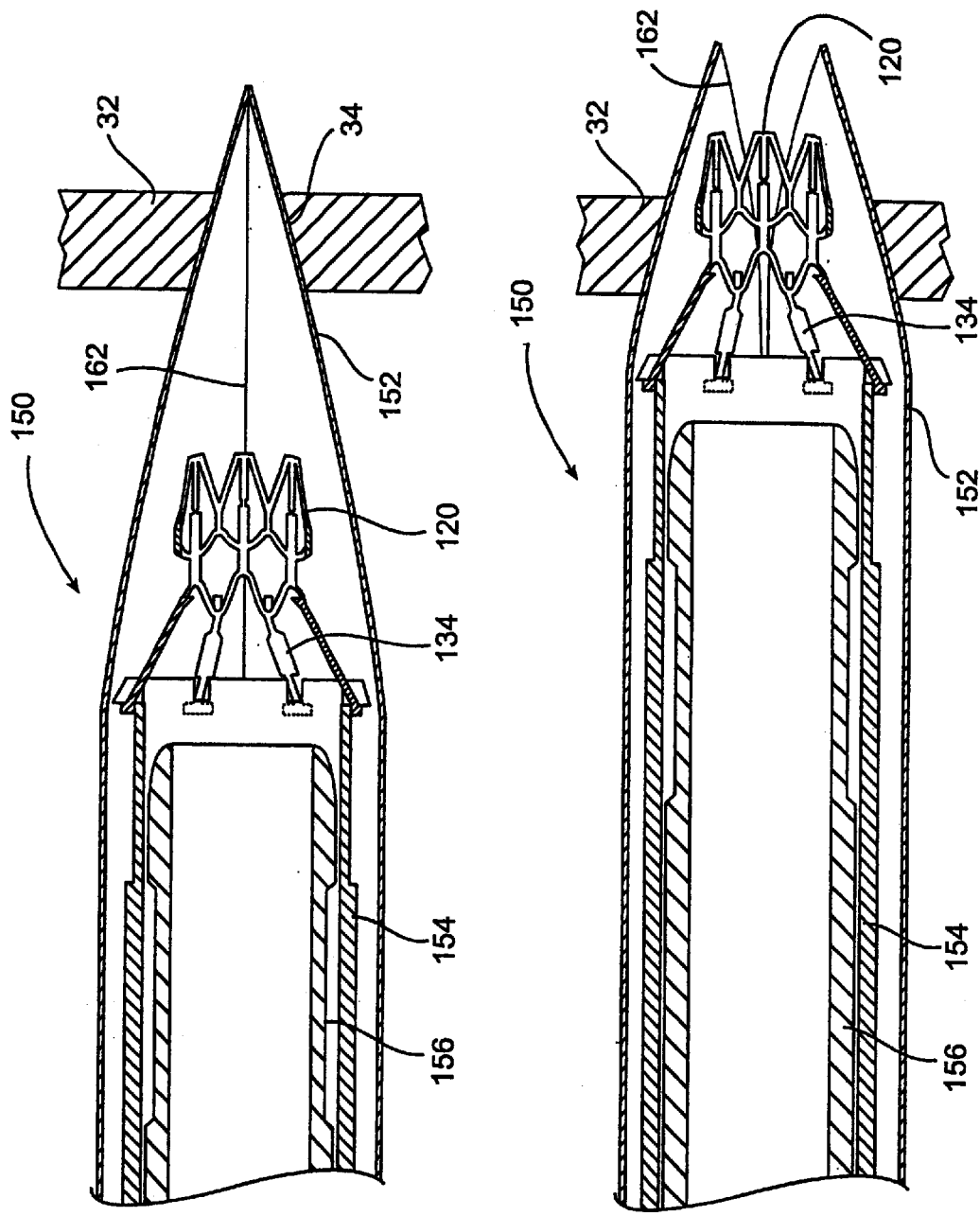

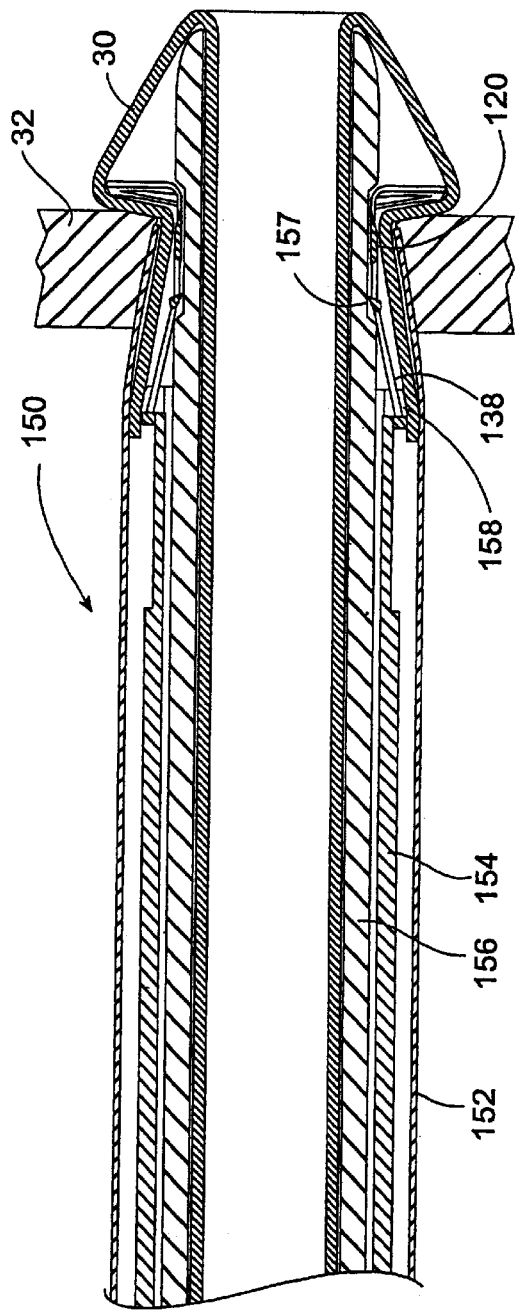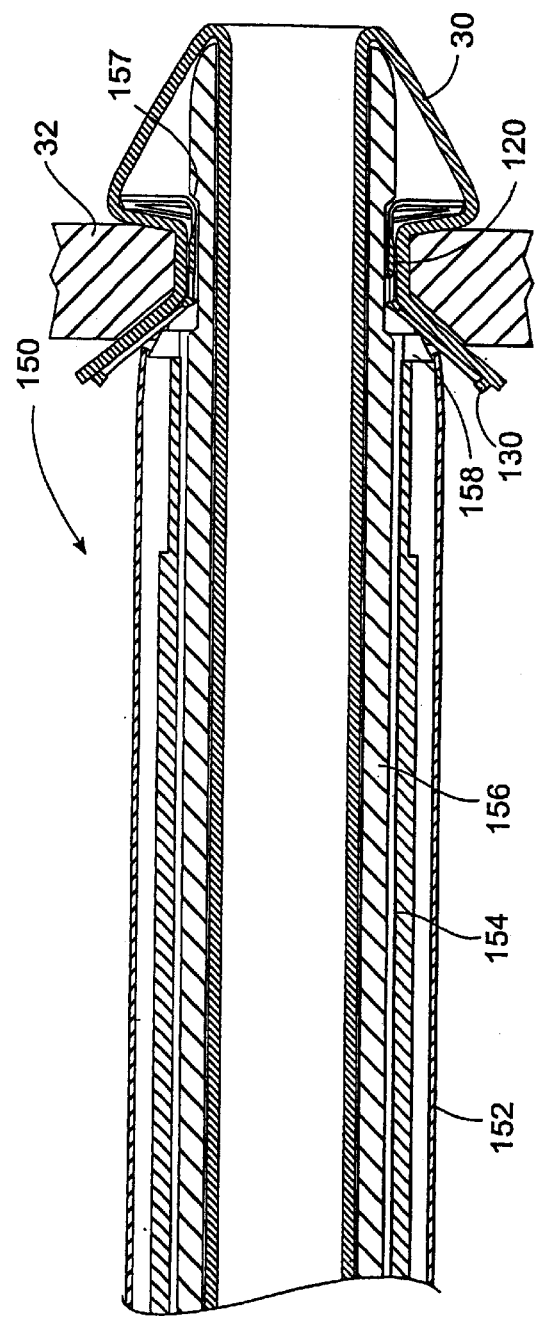

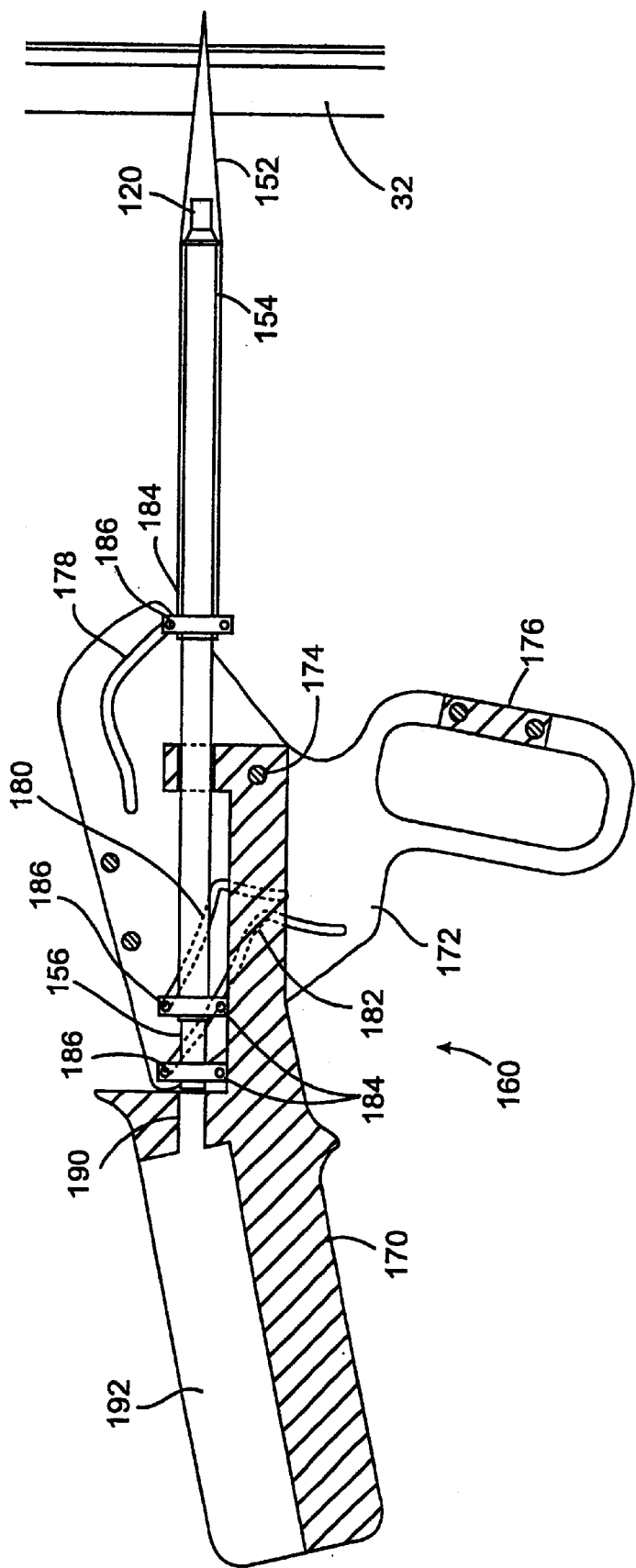

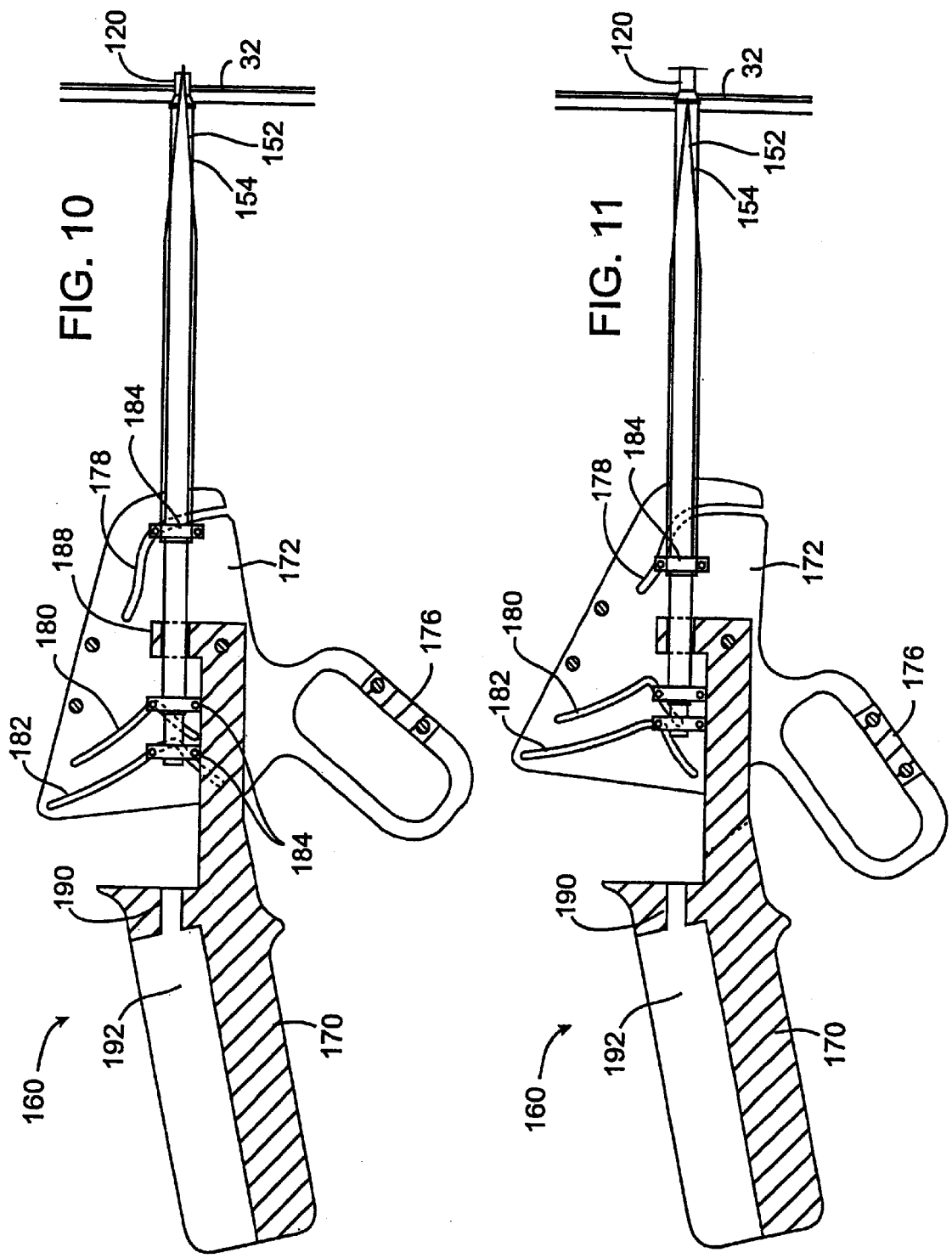

ns a continuation of application Ser. No.
09/437,428, filed on Nov. 15, 1999, which is a continuation-in-part of application Ser. No. 09/314,278, filed on May 18, 1999.

BACKGROUND OF THE INVENTION

1. Field of the Invention

The invention relates to an implantable medical device such as an anastomosis device and a deployment system for implanting the device. In a preferred embodiment, the device can be used for forming a sutureless connection between a bypass graft and a blood vessel.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patients blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

An additional problem with CABG is the formation of thrombi and atherosclerotic lesions at and around the grafted artery, which can result in the reoccurrence of ischemia. The thrombi and atherosclerotic lesions may be caused by the configuration of the sutured anastomosis site. For example, an abrupt edge at the anastomosis site may cause more stenosis than a more gradual transition.

Accordingly, it would be desirable to provide a sutureless vascular anastomosis device which easily connects a graft to a target vessel. It would also be desirable to provide a sutureless anastomosis device which is formed of one piece and is secured to the target vessel in a single step.

SUMMARY OF THE INVENTION

According to a preferred embodiment, the present invention relates to an anastomosis device for connecting an end of a graft vessel to a target vessel wherein the device cooperates with a deployment tool for connecting an end of the graft vessel to the target vessel. The anastomosis device comprises a first linkage deformable by the deployment tool to form a first flange (e.g., an inner flange which connects the graft vessel to an inner surface of the target vessel), an optional connecting portion extending from the first linkage, and a second linkage deformable by the deployment tool to form a second flange (e.g., an outer flange which connects the graft vessel to an outer surface of the target vessel), the second linkage including deformable links which cooperate with a distal end of the deployment tool to form the second flange. The anastomosis device is preferably sized to fit through an incision in the target vessel such that the first flange comprises an inner flange which presses a portion of the graft vessel into intimate contact with an inner surface of the target vessel and the second flange comprises an outer flange which presses another portion of the graft vessel into intimate contact with an outer surface of the target vessel.

The anastomosis device can include various features. For instance, a connecting portion can be provided between the first and second linkages and the first and second linkages can include axial members having weakened areas which cause the axial members to bend simultaneously during formation of the inner and/or outer flange. The deployment tool can include an expander which forms the first flange and a holder tube surrounding the expander, the holder tube engaging the deformable links and bending the deformable links outwardly to form the second flange.

The deployment tool can incorporate various features. For example, a deforming crown tool can include first members and the deformable links can include second members which remain connected to the first members during formation of the first flange and disconnect from the first members during formation of the second flange, the deformable members bending the deformable links outwardly during formation of the second flange and returning to a non-bent configuration after formation of the second flange. The first members can comprise tabs and the second members can comprise slots which engage the tabs and openings which disengage the tabs, the slots extending from the openings towards a proximal end of the anastomosis device. A deforming crown deployment tool can include deformable members at the distal end thereof, the deformable members being plastically deformed after bending the deformable links outwardly to form the second flange. In a third embodiment, the deployment tool breaks off part of the anastomosis device during formation of the outer flange. For example, the anastomosis device can include a deployed portion (implant) and a severable portion (discard) wherein the first and second flanges are formed on the deployed portion and the severable portion is severed from the deployed portion when the second flange is formed. The deployed portion can be connected to the severable portion by shearable connectors and the shearable connectors can be located at pivot connections between the deployed portion and the severable portion. The severable portion and the deployed portion are preferably machined from a single piece of metal and the pivot connections can comprise thin sections of the metal extending between the deployed portion and the severable portion.

The anastomosis device can incorporate various structural features. For instance, the first linkage can include a plurality of struts arranged in a configuration such that an axial dimension of the first linkage changes upon radial expansion of the first linkage. Further, the first linkage can include a plurality of piercing members which penetrate the graft vessel. The second linkage can include a plurality of axial members and struts arranged in a configuration such that radial expansion of the second linkage does not cause formation of the second flange. The second linkage can also include pairs of axial members which are closer together at a distal end thereof than at a proximal end thereof, the proximal ends of the axial members being joined by circumferentially extending severable links to a linkage supported by the tool, the severable links being severed when the second flange is formed.

An anastomosis device deployment system according to the invention can include a handle and a holder tube attached to the handle, the holder tube having a distal end configured to hold the anastomosis device with an attached graft vessel; and an expander positioned within the holder tube and slidable with respect to the holder tube to a position at which the expander is positioned within the anastomosis device and radially expands the anastomosis device. The system can further include a trocar movable with respect to the holder tube to form an opening in a target vessel to receive the anastomosis device and attached graft vessel. The trocar can be a split trocar which is slidable over the holder tube and the expanded anastomosis device. The handle can include cam grooves which cooperate with followers of the holder tube and expander to move the holder tube and expander with respect to one another upon activation of a trigger of the handle. The distal end of the holder tube can include a plurality of slits, loops and/or flexible fingers for engaging tabs of the anastomosis device during formation of the inner and outer flanges.

According to another embodiment of the invention, the frangible linkage can be used to release an implant portion of a medical device at a target site in a living body. According to this embodiment, the medical device cooperates with a deployment tool for delivering and deploying the medical device to the site. The medical device includes first and second sections connected together by a frangible linkage, the frangible linkage being deformable by the deployment tool such that frangible elements of the frangible linkage are broken and the first section is separated from the second section. The frangible elements can include weakened areas which cause the frangible elements to bend when the frangible linkage is deformed by the deployment tool. For instance, the medical device can comprise an anastomosis device and the first section can include hinged axial members which bend outwardly and form first and second flanges. The deployment tool can include an expander which forms the first flange and a holder tube surrounding the expander, the holder tube engaging the second section and forming the second flange while separating the first section from the second section.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 3 is a perspective view of an anastomosis device deployment system;

FIG. 4 is an enlarged perspective view of the distal end of the anastomosis device deployment system of FIG. 3 with an anastomosis device prior to deployment;

FIG. 5 is a side cross sectional view of the anastomosis device deployment system puncturing the target vessel to advance the anastomosis device into the target vessel wall;

FIG. 6 is a side cross sectional view of the anastomosis device deployment system advancing the anastomosis device into the target vessel wall;

FIG. 7 is a side cross sectional view of the anastomosis device deployment system with an expanded first annular flange;

FIG. 8 is a side cross sectional view of the anastomosis device deployment system expanding a second annular flange;

FIG. 9 is a schematic side cross-sectional view of a deployment tool taken along line A—A of FIG. 3, the deployment tool is shown during a vessel puncturing step;

FIG. 10 is a schematic side cross-sectional view of the deployment tool of FIG. 9 shown during an anastomosis device insertion step;

FIG. 11 is a schematic side cross-sectional view of the deployment tool of FIG. 9 shown during an anastomosis device expansion step;

DETAILED DESCRIPTION OF THE PREFERRED EMBODIMENTS

Figure 1:
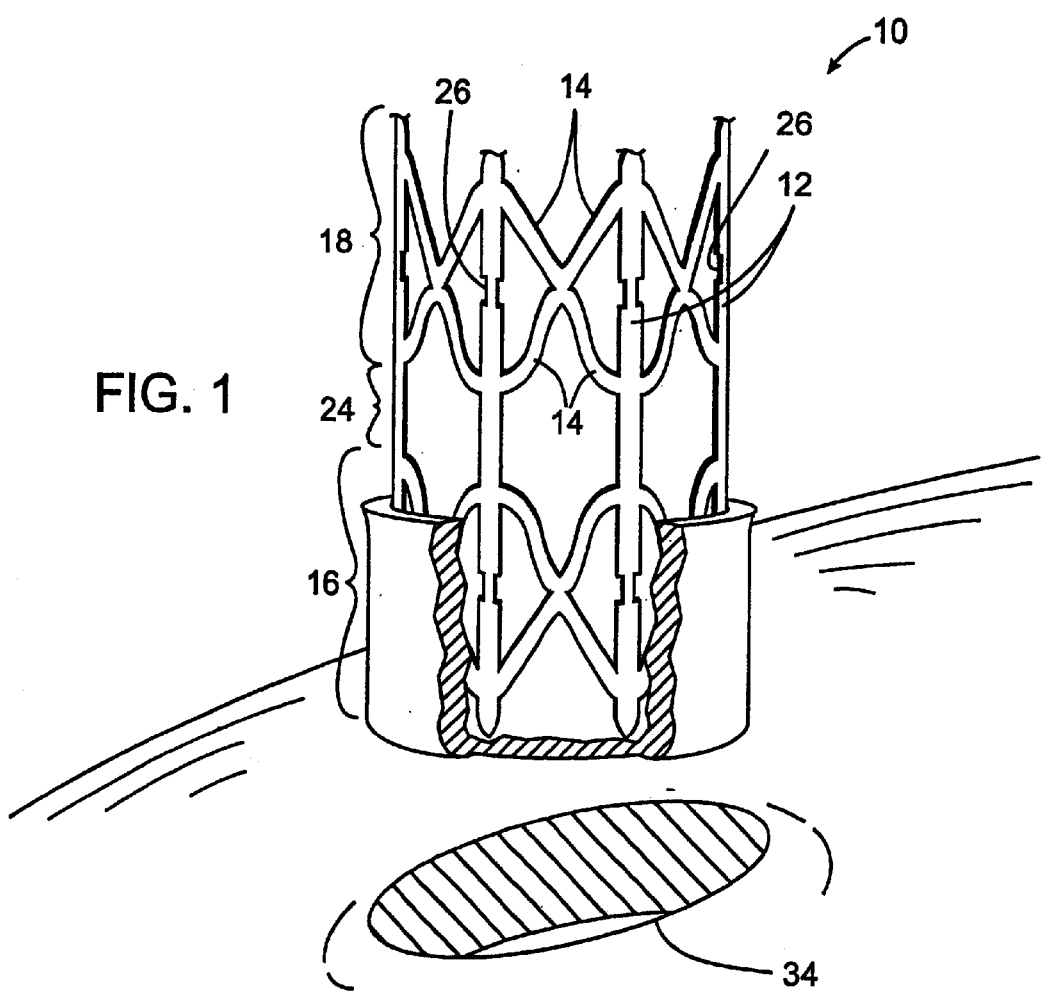
FIG. 1 is a perspective view of a first embodiment of an anastomosis device in a configuration prior to use with a graft vessel everted over the device.

According to the invention it is possible to perform a variety of anastomosis procedures, including coronary artery bypass grafting. The term "target vessel" is thus used to refer to vessels within the patient which are connected to either or both of the upstream and downstream end of the graft vessel. In such procedures, a large vessel anastomotic device is used with large diameter target vessels such as the aorta or its major side branches or a small vessel anastomotic device is used for a target vessel which has a small diameter such as a coronary artery.

In deploying a large vessel anastomotic device, the device (with one end of a graft vessel attached thereto) is inserted into an incision in a wall of the target vessel with a deformable section in a first configuration, and the deformable section is radially expanded to a second configuration to deploy a flange. The flange applies an axial force against the wall of the target vessel. Additionally, the flange can be configured to apply a radial force, substantially transverse to the device longitudinal axis, against the wall of the target vessel, to secure the device to the target vessel. For example, the device can have a plurality of deformable sections forming distal and proximal flanges. With the proximal and distal end flanges deployed, the device can be prevented from shifting proximally out of the target vessel or distally further into the interior of the target vessel.

The large vessel devices can be configured to connect to target vessels of various sizes having a wall thickness of at least about 0.5 mm, and typically about 0.5 mm to about 5 mm. In a preferred embodiment of the invention, the large vessel anastomotic device is configured to longitudinally collapse as the deformable section is radially expanded. The surgeon can control the longitudinal collapse to thereby position the distal end flange at a desired location at least partially within the incision in the target vessel wall. The surgeon can also control the position of the proximal end flange by longitudinally collapsing the device to a greater or lesser degree, to thereby position the proximal end flange at a desired location in contact with the target vessel. Thus, regardless of the thickness of the target vessel wall, the device can be longitudinally collapsed to position the flanges against the target vessel wall and effectively connect the device thereto. This feature is significant because the device must be connected to target vessels which have a wide range of wall thickness. For example, the aortic wall thickness is typically about 1.4 mm to about 4.0 mm and the aorta diameter can range from about 25 to about 65 mm in diameter. Therefore, regardless of the thickness of the target vessel wall, the degree of deployment of the proximal end flange, and thus the longitudinal collapse of the device, can be controlled by the physician to thereby effectively connect the device to the target vessel. For example, the surgeon may choose between partially deploying the proximal end flange so that it is positioned against an outer surface of the target vessel wall, or fully deploying the flange to position it in contact with the media of the target vessel wall within the incision in the target vessel wall.

In deploying a small vessel anastomotic device, the device can be used on small target vessels having a wall thickness of less than about 1.0 mm, and typically about 0.1 mm to about 1 mm in the case of coronary arteries. Despite the small size of the target vessels, the small vessel devices provide sutureless connection without significantly occluding the small inner lumen of the target vessel or impeding the blood flow therethrough. For example, the small vessel devices can include an outer flange (with the graft vessel connected thereto) loosely connected to an inner flange before insertion into the patient with the space between the loosely connected inner and outer flanges being at least as great as the wall thickness of the target vessel so that the inner flange can be inserted through an incision in the target vessel and into the target vessel lumen, with the outer flange outside the target vessel. With the outer and inner flanges in place on either side of a wall of the target vessel, tightening the flanges together compresses a surface of the graft vessel against the outer surface of the target vessel. This configuration forms a continuous channel between the graft vessel and the target vessel, without the need to suture the graft vessel to the target vessel wall and preferably without the use of hooks or barbs which puncture the target vessel.

In a coronary bypass operation in accordance with the invention, a large vessel device can be used to connect the proximal end of the graft vessel to the aorta, and a small vessel device can be used to connect the distal end of the graft vessel to an occluded coronary artery. However, in patients with an extreme arteriosclerotic lesion in the aorta, which may result in serious complications during surgical procedures on the aorta, the surgeon may wish to avoid this region and connect the proximal end of the graft vessel to any other adjacent less diseased vessel, such as the arteries leading to the arms or head. Further, the devices can be used with venous grafts, such as a harvested saphenous vein graft, arterial grafts, such as a dissected mammary artery, or a synthetic prosthesis, as required.

Connection of the large vessel device does not require the stoppage of blood flow in the target vessel. Moreover, the anastomotic devices can be connected to the target vessel without the use of cardiopulmonary bypass. In contrast, anastomosis techniques wherein the aorta is clamped to interrupt blood flow to the area of the aortic wall to which a vein is to be anastomosed may result in liberation of plaques and tissue fragments which can lead to organ dysfunction, such as strokes, renal failure, or intestinal ischemia. However, severely diseased aortas may not provide an area suitable for clamping due to significant calcification of the aortic wall. In the anastomosis technique according to the invention, the surgeon does not need significant room inside the patient to connect the anastomotic devices to the target vessel. For example, unlike sutured anastomoses which require significant access to the aorta for the surgeon to suture the graft vessel thereto, the anastomotic devices allow the proximal end of the graft vessel to be connected to any part of the aorta. All parts of the aorta are accessible to the large vessel anastomosis devices, even when minimally invasive procedures are used. Consequently, the graft vessel may be connected to the descending aorta, so that the graft vessel would not be threatened by damage during a conventional sternotomy if a second operation is required at a later time.

According to the invention, a sutureless connection can be provided between a graft and a target vessel, while minimizing thrombosis or restenosis associated with the anastomosis. The anastomotic devices can be attached to the target vessel inside a patient remotely from outside the patient using specially designed applicators, so that the devices are particularly suitable for use in minimally invasive surgical procedures where access to the anastomosis site is limited. The devices allow the anastomosis to be performed very rapidly, with high reproducibility and reliability, without clamping, and with or without the use of cardiopulmonary bypass.

According to one preferred method of deploying the anastomosis device, the surgeon operates a deployment tool using both hands. One hand supports the tool via a handle while the other twists an actuation knob to deploy the anastomotic device. Locating the actuation knob on the tool's main axis minimizes the tendency of reaction forces to wobble the tool keeping it stable and in proper position during deployment. The twisting motion is converted to linear displacements by a set of rotating cams that engage a trocar, holder, and expander. The cams control the sequence of relative motions between the instrument's trocar and device deployment mechanisms.

During the foregoing procedure, a surgeon will place the tip of the instrument (the mechanical stop) in light contact with the site on the aorta to be anastomosed. Having located a suitable site, the surgeon then twists the actuation knob to fire the spring-loaded trocar and continues twisting to deploy the anastomotic device. The trocar penetrates the aortic wall at a high rate of speed to minimize any unintended deformation of the aorta and maintains a substantially fluid-tight seal at the puncture site. Having entered the aortic lumen, the trocar dilates as the anastomotic device and its holder tube (crown) are advanced through it, thus retracting the aortic tissue and serving as an introducer for the device. Once the device has fully entered the aortic lumen the trocar is withdrawn. The anastomotic device is then expanded to its full diameter and an inner flange is deployed. The device is then drawn outwards towards the instrument (mechanical stop) to seat the inner flange firmly against the intimal wall of the aorta. An outer flange is then deployed from the external side, compressing the aortic wall between the inner and outer flanges and the device is disengaged from the instrument completing the anastomosis.

Figure 2:
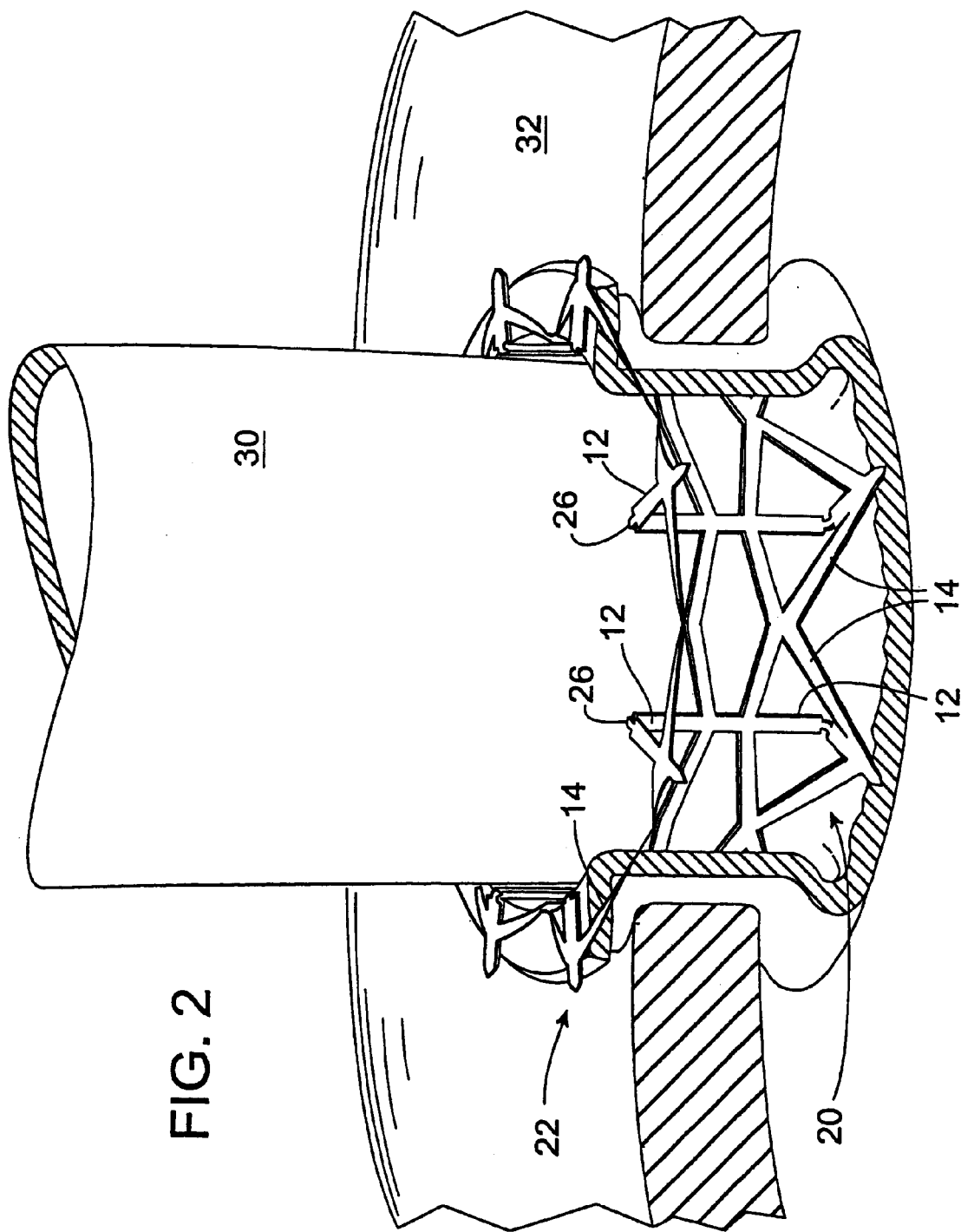
FIG. 2 is a perspective view of the anastomosis device of FIG. 1 in a deployed configuration.

FIG. 1 illustrates the distal portion of an anastomosis device 10 according to a first embodiment of the present invention, the proximal portion (not shown) being adapted to be deployed by a deployment tool which will be explained later. The anastomosis device 10 includes a plurality of axial members 12 and a plurality of struts 14 interconnecting the axial members. The axial members 12 and struts 14 form a first linkage 16 at a first end of the device and a second linkage 18 at a second end of the device. The first and second linkages 16, 18 form inner and outer flanges 20, 22 when the anastomosis device 10 is deployed as illustrated in FIG. 2. The deployed flanges 20, 22 may be annular ring shaped or conical in shape. The first and second linkages 16, 18 are connected by a central connecting portion 24.

In use, a graft vessel 30 is inserted through a center of the tubular anastomosis device 10 and is everted over the first linkage 16 at the first end of the device. The first end of the device may puncture part way or all the way through the graft vessel wall to hold the graft vessel 30 on the device. An opening 34 is formed in the target vessel 32 to receive the graft vessel 30 and anastomosis device 10. Once the anastomosis device 10 with everted graft vessel 30 are inserted through the opening 34 in the target vessel 32, the inner and outer flanges 20, 22 are formed as shown in FIG. 2 to secure the graft vessel to the target vessel by trapping the wall of the target vessel between the two flanges. The anastomosis device 10 forms a smooth transition between the target vessel 32 and the graft vessel 30 which helps to prevent thrombi formation.

The inner and outer flanges 20, 22 are formed by radial expansion of the anastomosis device 10 as follows. The first and second linkages 16, 18 are each made up of a plurality of axial members 12 and struts 14. The struts 14 are arranged in a plurality of diamond shapes with adjacent diamond shapes connected to each other to form a continuous ring of diamond shapes around the device. One axial member 12 extends through a center of each of the diamond shapes formed by the struts 14. A reduced thickness section 26 or hinge in each of the axial members 12 provides a location for concentration of bending of the axial members. When an expansion member of a deployment tool such as a rod or balloon is inserted into the tubular anastomosis device 10 and used to radially expand the device, each of the diamond shaped linkages of struts 14 are elongated in a circumferential direction causing a top and bottom of each of the diamond shapes to move closer together. As the top and bottom of the diamond shapes move closer together, the axial members 12 bend along the reduced thickness sections 26 folding the ends of the device outward to form the inner and outer flanges 20, 22 with the result that the wall of the target vessel 32 is trapped between the flanges and the everted graft vessel 30 is secured to the target vessel.

In the anastomosis device 10 shown in FIGS. 1 and 2, the struts 14 may be straight or curved members having constant or varying thicknesses. In addition, the axial members 12 may have the reduced thickness sections 26 positioned at a center of each of the diamond shapes or off center inside the diamond shapes. The positioning and size of the reduced thickness sections 26 will determine the location of the flanges 20, 22 and an angle the flanges make with an axis of the device when fully deployed. A final angle between the flanges 20, 22 and longitudinal axis of the device 10 is about 40–100 degrees, preferably about 50–90 degrees.

FIGS. 3–7 illustrate a deployment system 150 and sequence of deploying an anastomosis device 120 such as the device shown in FIGS. 1–2 with the deployment system. In FIGS. 3–5 the graft vessel 30 has been eliminated for purposes of clarity. As shown in FIGS. 3–7, the deployment system 150 includes a hollow outer trocar 152 (not shown in FIG. 3), a holder tube 154 positioned inside the trocar, and an expander tube 156 slidable inside the holder tube. As can be seen in the detail of FIG. 4, the anastomosis device 120 is attached to a distal end of the holder tube 154 by inserting T-shaped ends 112 of pull tabs 110 in slots 158 around the circumference of the holder tube. The trocar 152, holder tube 154, and expander tube 156 are all slidable with respect to one another during operation of the device. A device handle 160 is provided for moving the tubes with respect to one another will be described in further detail below with respect to FIGS. 8–11.

As shown in FIG. 5, initially, the holder tube 154, expander tube 156, and the anastomosis device 120 are positioned within the trocar 152 for insertion. The trocar 152 has a hollow generally conical tip with a plurality of axial slots 162 which allow the conical tip to be spread apart so that the anastomosis device 120 can slide through the opened trocar. The trocar 152, acting as a tissue retractor and guide, is inserted through the wall of the target vessel 32 forming an opening 34. As shown in FIG. 6, the anastomosis device 120 is then advanced into or through the target vessel wall 32 with the holder tube 154. The advancing of the holder tube 154 causes the distal end of the trocar 152 to be forced to spread apart. Once the anastomosis device 120 is in position and the trocar 152 has been withdrawn, the inner annular flange 20 is deployed by advancing the expander tube 156 into the anastomosis device. The advancing of the expander tube 156 increases the diameter of the anastomosis device 120 causing the inner flange to fold outward from the device. This expanding of the inner flange may be performed inside the vessel and then the device 120 may be drawn back until the inner flange abuts an interior of the target vessel wall 32.

As shown in FIG. 8, after the inner flange has been deployed, the holder tube 154 is advanced forming the outer flange. As the holder tube 154 is advanced, the anastomosis device 120 drops into a radial groove 157 on an exterior of the expander tube 156 which holds the anastomosis device stationary on the expander tube 156. The holder tube 154 is then moved forward to detach the entire anastomosis device by disengaging the pull tabs 130 from the slots 158 in the holder tube and causing the outer flange to be deployed. During deployment of the outer flange, shoulders 134 on the device, shown most clearly in FIGS. 5 and 6, engage a tapered distal end of the holder tube 154 causing the pull tabs 130 to be released from the slots 158. Alternatively, and as will be explained in connection with a frangible anastomosis device according to the invention, movement of the holder tube 154 can detach a deployed portion of the device from a discard portion of the device which remains attached to the holder tube.

One alternative embodiment of the holder tube 154 employs a plurality of flexible fingers which receive the pull tabs 130 of the anastomosis device 120. According to this embodiment each pull tab 130 is received by an independent finger of the holder tube 154. To deploy the second or outer flange of the anastomosis device 120, the flexible fingers flex outward bending the pull tabs 130 outward. For instance, the flexible fingers can be designed to flex when the pull tabs and fingers are put under axial compression in which case the fingers and tabs buckle outwards together to deploy the outer flange and release the anastomosis device from the holder tube.

FIGS. 9–12 illustrate the operation of the handle 160 to move the trocar 152, the holder tube 154, and the expander tube 156 with respect to one another to deploy the anastomosis device 120 according to the present invention. The handle 160 includes a grip 170 and a trigger 172 pivotally mounted to the grip at a pivot 174. The trigger 172 includes a finger loop 176 and three contoured cam slots 178, 180, 182 corresponding to the trocar 152, holder tube 154, and expander tube 156, respectively. Each of these tubes has a fitting 184 at a distal end thereof. A pin 186 connected to each of the fittings 184 slides in a corresponding one of the cam slots 178, 180, 182. A fourth cam slot and tube may be added to control deployment of the outer flange. Alternatively, the handle can be modified to include fewer cam slots for deployment of the inner and outer flanges.

The handle 160 is shown in FIG. 8 in an insertion position in which the trocar 152 extends beyond the holder tube 154 and the expander tube 156 for puncturing of the target vessel wall 32. Optionally, a flexible seal (not shown) such as heat shrinkable plastic or elastomeric tubing can be provided on the outer surface of the trocar 152 such that the seal covers the axial slots 162 at a location spaced from the tip of the trocar to prevent leaking of blood from the target vessel after the incision is formed. In a preferred embodiment, the trocar is actuated by a mechanism which causes the trocar to penetrate the aorta wall at a high rate of speed to minimize deformation of the aorta and maintain a fluid tight seal at the puncture site in a manner similar to biopsy gun. For instance, the spring mechanism attached to the trocar and/or the handle can be used to fire the trocar at the incision site. Any suitable actuating mechanism can be used to fire the trocar in accordance with the invention. As the trigger 172 is rotated from the position illustrated in FIG. 9 to the successive positions illustrated in FIGS. 10–12, the pins 186 slide in the cam slots 178, 180, 182 to move the trocar 152, holder tube 154 and expander tube 156.

FIG. 10 shows the handle 160 with the trigger 172 rotated approximately 30 degrees from the position of FIG. 9. This rotation moves the holder tube 154 and expander tube 156 forward into the wall of the target vessel 32 spreading the trocar 152. The anastomosis device 120 is now in position for deployment. FIG. 11 shows the trigger 172 rotated approximately 45 degrees with respect to the position of FIG. 9 and the cam slot 182 has caused the expander tube 156 to be advanced within the holder tube 154 to deploy the inner flange. The trocar 152 has also been withdrawn.

Figure 12:
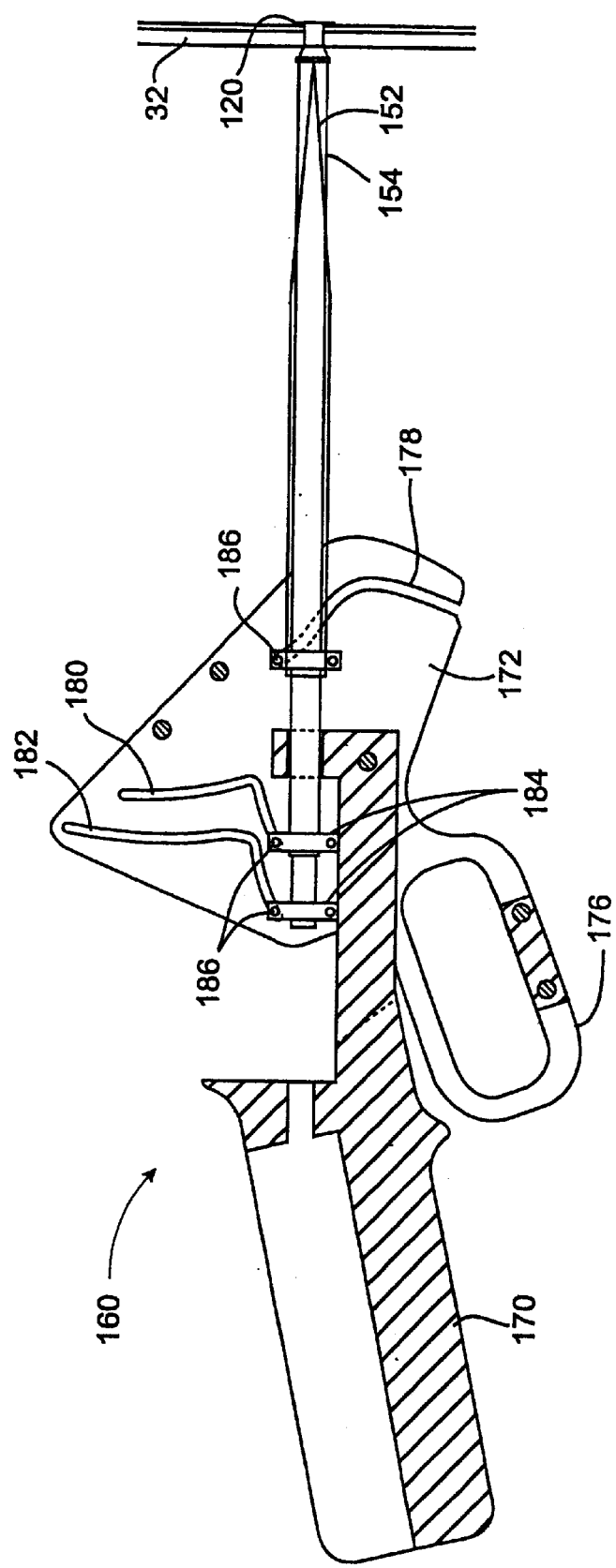
FIG. 12 is a schematic side cross-sectional view of the deployment tool of FIG. 9 shown after the anastomosis device has been fully deployed.

FIG. 12 shows the handle 160 with the trigger 172 pivoted approximately 60 degrees with respect to the position shown in FIG. 9. As shown in FIG. 12, the expander tube 156 has been withdrawn to pull the inner flange against the vessel wall 32 and the holder tube 154 is moved forward to deploy the outer flange and disengage the holder tube 154 from the anastomosis device 120.

The handle 160 also includes a first channel 188 and a second channel 190 in the grip 170 through which the graft vessel (not shown) may be guided. The grip 170 also includes a cavity 192 for protecting an opposite end of the graft vessel from the attachment end.

According to one embodiment of the invention, the anastomosis device includes a frangible linkage which allows an implant to separate from the remainder of the device upon formation of the outer flange. According to a preferred linkage design, the frangible linkage can be radially expanded and axially compressed to fracture the frangible linkage. The inner flange can be formed during radial expansion of the device and the implant can be severed while forming the outer flange.

Figure 13:
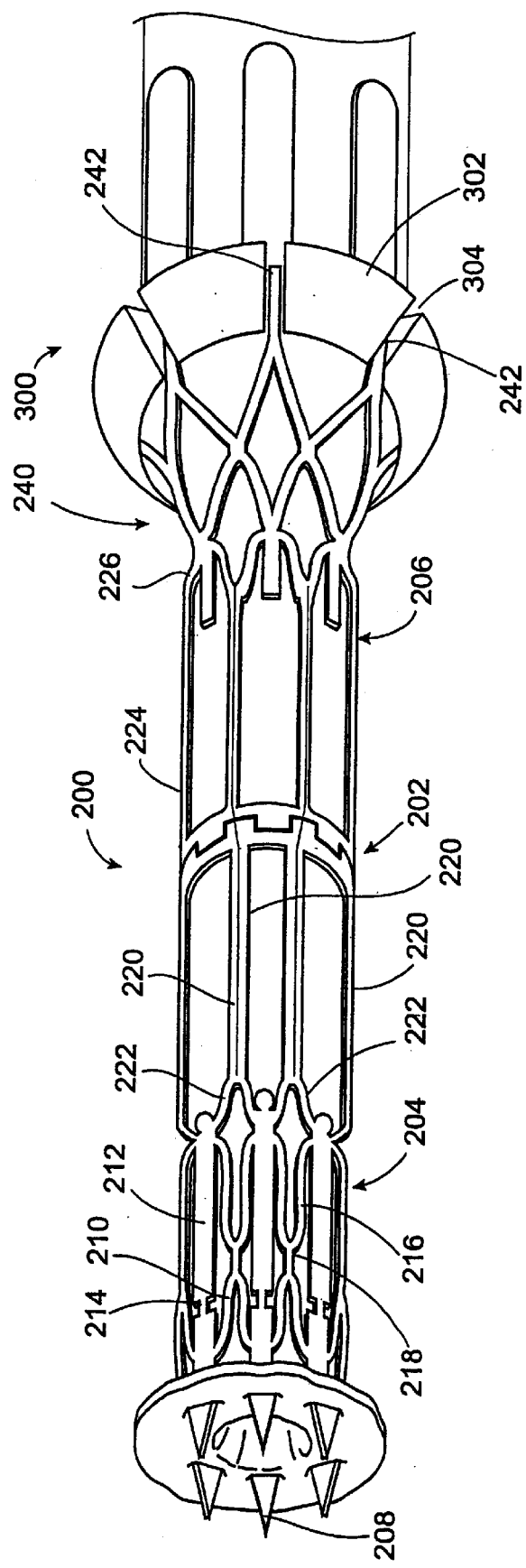
FIG. 13 is a perspective view of a frangible anastomosis device in a configuration prior to use.

FIG. 13 shows a device 200 which cooperates with a deployment tool 300 for delivering and deploying an implant 204 at a site in a living body. The device includes a frangible linkage 202 connecting the implant 204 to a discard portion 206. As explained below, after the device is positioned at a desired location, the implant 204 can be expanded to deploy an inner flange and subsequently axially compressed to deploy an outer flange while severing the implant 204 from the discard portion 206. The deployment tool can then be withdrawn along with the discard portion 206 which remains attached to the distal end of the deployment tool 300.

Figure 14:
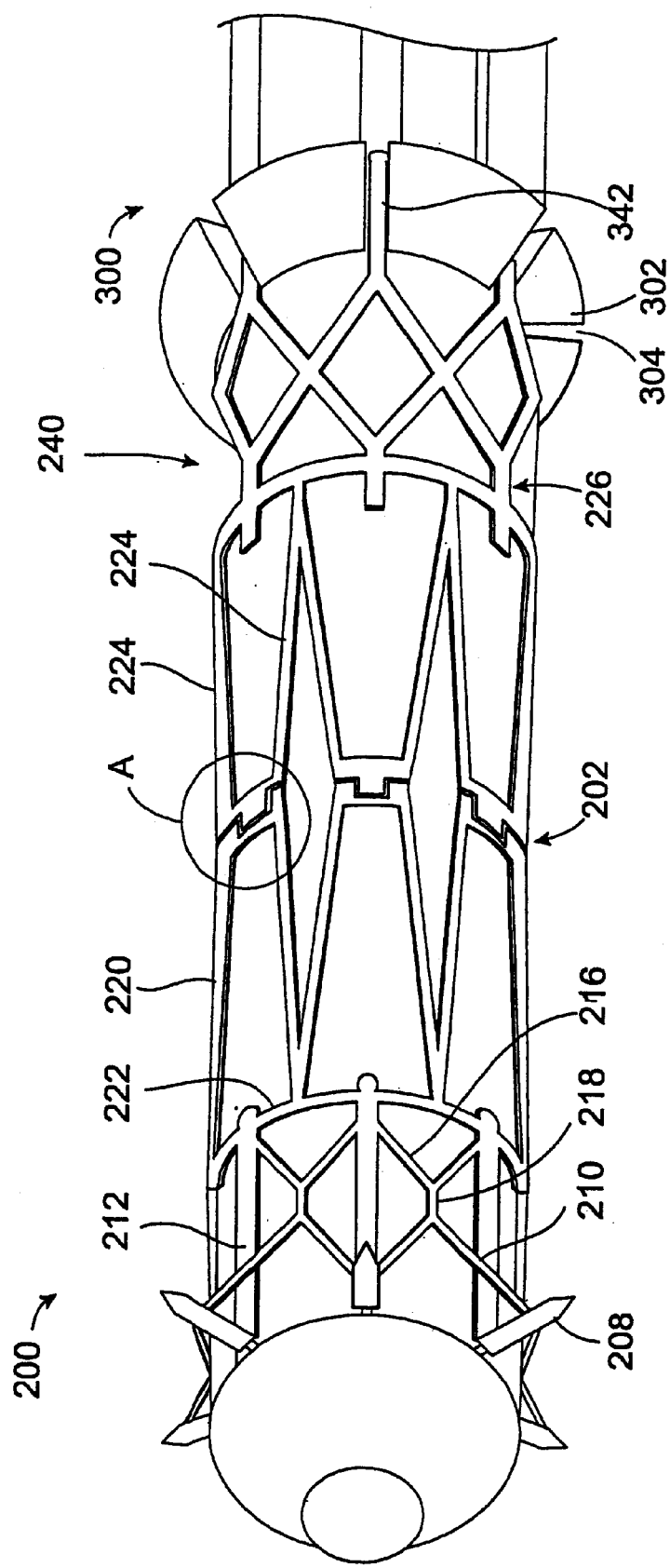
FIG. 14 is a perspective view of the device shown in FIG. 13 after radial expansion thereof.

FIG. 14 shows the device 200 in the radially expanded condition but prior to being axially compressed. During radial expansion of the device, axially extending barbs 208 (FIG. 13) are pivoted outwardly by struts 210 such that the outwardly extending barbs 208 and struts 210 form the inner flange. To facilitate bending of the barbs, the barbs 208 comprise points on the ends of axially extending members 212 which have narrow sections 214 located a desired distance from the free ends of the barbs 208. For instance, the narrow sections 214 can be located at axial positions along the device corresponding approximately to the axial midpoint of the struts 210 connecting adjacent members 212 when the device is in the pre-expanded condition shown in FIG. 13.

To facilitate easier bending of the struts 210 during radial expansion of the device, the distal ends of the struts can be curved at their points of attachment to the members 212. Likewise, a curved bend can be provided at the intersection where the proximal ends of the struts are attached together. When the device is radially expanded, the members 212 move radially outward and circumferentially apart as the struts 210 move radially outward until a force on the barbs 208 by the struts 210 causes the struts to become bent at the narrow sections 214, after which the barbs extend outwardly to form the inner flange. In this deployed condition, the barbs 208 are locked into position by an X-shaped frame formed by struts 210 and additional struts 216. The struts 216 are similar in configuration to the struts 210 with respect to how they are shaped and attached to the members 212. Short axially extending members 218 connect the intersection of the struts 210 to the intersection of the struts 216.

The frangible section 202 is located at the proximal ends of axially extending members 220 which are connected to the members 212 by U-shaped links 222. The members 220 are arranged in pairs which are attached together at only their distal ends. In particular, the distal ends of the links 222 are attached to proximal ends of the members 212 and the midpoint of each link 222 is attached to the distal ends of a respective pair of members 220. As shown in FIG. 14, during radial expansion of the device, the individual links 222 are plastically deformed from their U-shaped configuration to form segments of a circumferentially extending annular ring. As a result, the device becomes shorter in the axial direction as links 222 form the annular ring and the distal ends of the members 220 move radially outward but not apart in the circumferential direction. At the same time, the proximal ends of the members 220 move radially outward and circumferentially apart.

Figure 15:
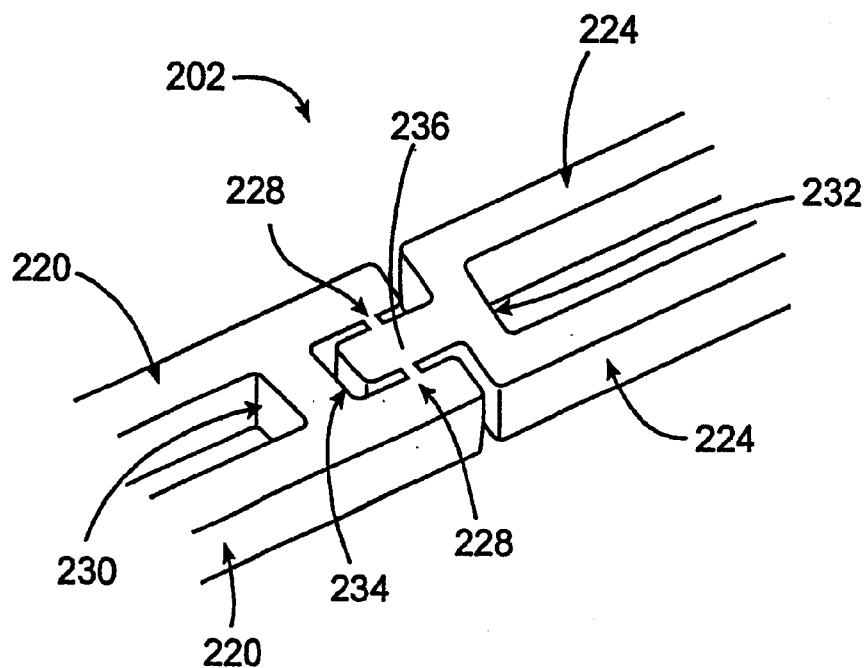
FIG. 15 shows a frangible link from the portion of FIG. 14 within the circle labeled A.
Figure 16:
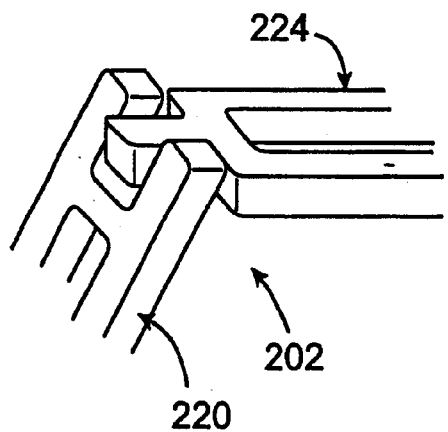
FIG. 16 shows the frangible link of FIG. 15 in a bent configuration.

FIG. 15 shows an expanded view of the circled portion A in FIG. 14 and FIG. 16 shows how the frangible section 202 can be bent to fracture connection points between members 220 and axial extending members 224. As shown in FIGS. 14 and 15, proximal ends of the members 224 are attached to U-shaped links 226 which allow the proximal ends of the members 224 to move radially outward but not circumferentially apart when the device is expanded. As shown in FIG. 15, the distal ends of members 224 and connected to the proximal ends of the members 220 by a frangible joint comprised of shearable connections 228. In the embodiment shown, the members 220 are connected at their proximal ends by a cross piece 230 and the members 224 are connected at their distal ends by a cross piece 232. The cross piece 230 includes a recess 234 and the cross piece 232 includes a projection 236 located in the recess 234. The frangible joint is preferably formed from a unitary piece of material (e.g., stainless steel, nickel titanium alloy, etc.) such as a laser cut tube wherein the shearable connections 228 comprise thin sections of material extending between opposite sides of the projection 236 and opposing walls of the recess 234. As shown in FIG. 16, the recess 234 contains the projection 236 as the members 220 and 224 are pivoted about the joint formed by the shearable connections 228. When the members 220 and 224 are pivoted to a sufficient extent, the shearable connections 228 are fractured allowing the implant to separate from the discard portion of the device.

Figure 17:
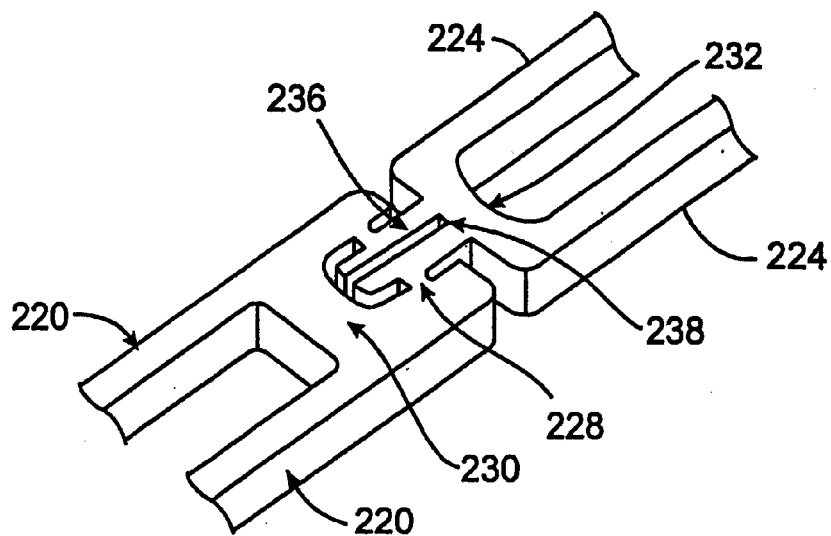
FIG. 17 shows a variation of the frangible link shown in FIG. 15.
Figure 18:
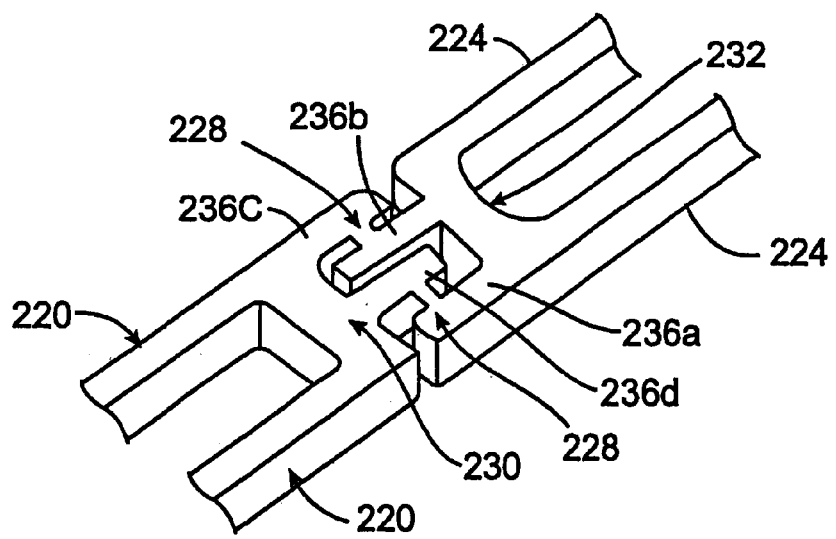
FIG. 18 shows another variation of the frangible link shown in FIG. 15.

The frangible link shown in FIGS. 15–16 can be modified in various ways. For instance, as shown in FIG. 17, the projection can have a slot 238 extending from the free end thereof towards cross piece 232. The slot 238 allows the portions of the projection on either side of the slot 238 to move closer together as the proximal ends of members 224 bend away from each other during radial expansion of the device 200. Likewise, the proximal ends of the members 220 on either side of the projection 236 can move closer together as the distal ends of the members 220 move apart during the radial expansion. Another variation is shown in FIG. 18 wherein two projections 236a and 236b extend from cross piece 232 and two projections 236c and 236d extend from cross piece 230, projections 236a and 236d being connected by a first shearable connection 228 and projections 236c and 236d being connected by a second shearable connection 228. As with the arrangement in FIG. 17, the arrangement in FIG. 18 allows the projections 236a–d to become squeezed together during radial expansion of the device 200.

The device 200 can be deployed using deployment tool 300 as follows. As shown in FIGS. 13 and 14, the device 200 includes a crown 240 attached to a distal end 302 of the tool 300. The crown includes axially extending members 242 with tabs (not shown) on the proximal ends thereof, the members 242 being held in slots 304 of the tool 300 by the tabs. A plastic sleeve (not shown) can be placed over the slots 304 to prevent the members 242 from coming out of the slots. As shown in FIG. 13, the crown is flared outwardly such that the members 242 are fully radially expanded at their proximal ends. During radial expansion of the device 200, the diamond shaped linkage of the crown 240 is expanded from the configuration shown in FIG. 13 to the expanded configuration shown in FIG. 14.

In the embodiment shown in FIGS. 13–14, the device 200 is attached to the tool 300 in a manner such that the discard portion 206 stays with the tool during deployment of the implant 204 and removal of the tool from the implant site. As previously described, the discard can include tabbed members fitted in grooves of the tool. Other suitable attachment techniques include welding the proximal end of the device to the tool using resistance welding, ultrasonic welding or the like, molding the proximal end of the device into the distal end of the tool such as by insert molding, mechanically fastening the proximal end of the device to the tool, adhesive bonding, etc.

Figure 19:
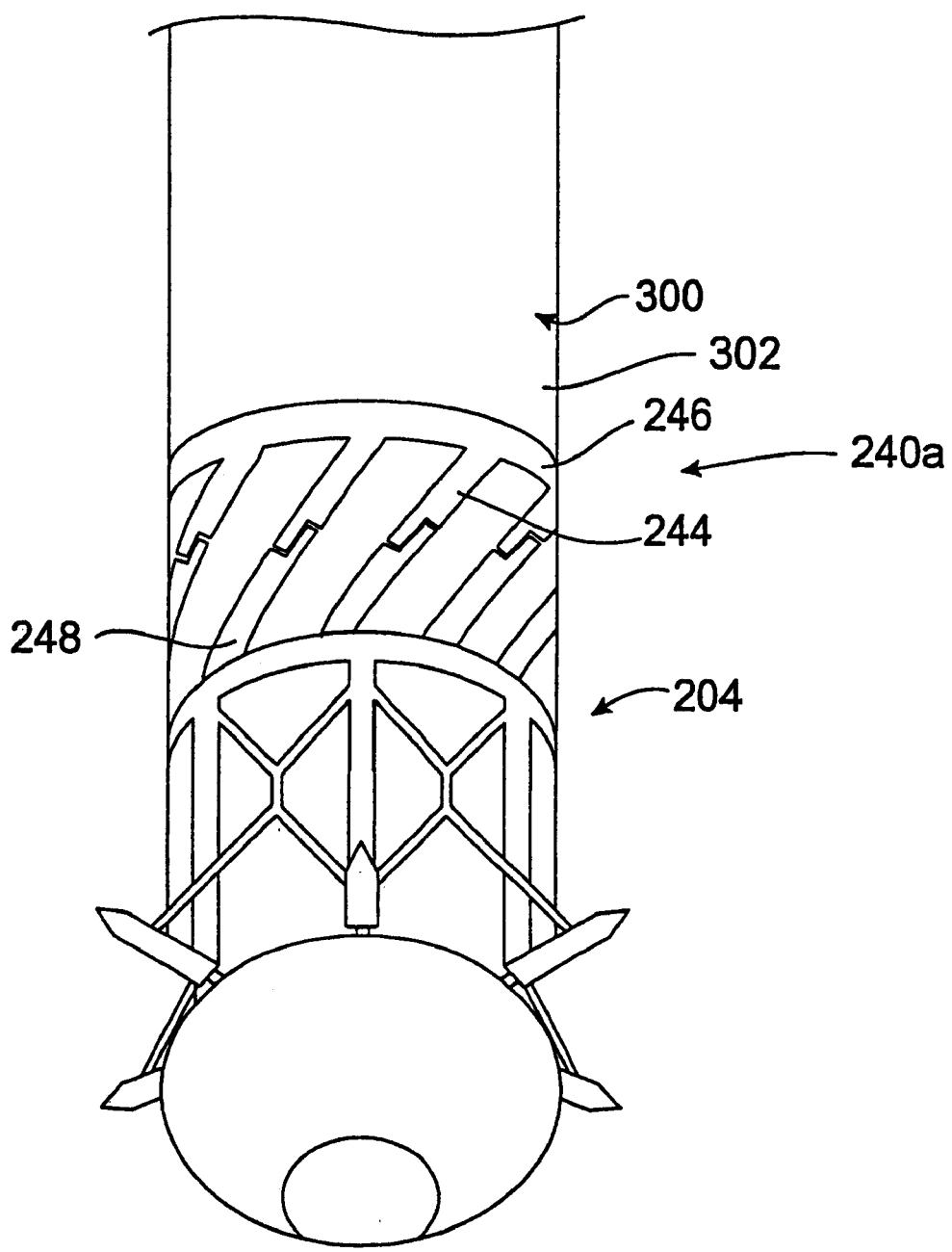
FIG. 19 shows a deforming crown design wherein the outer flange of the device is formed from frangible helical members.

In the foregoing embodiment, the device is deployed by radial expansion and axial compression. The axial compression can be accomplished by pushing the holder tube while the expander tube is held in a fixed position or vice versa. According to a further embodiment, the axial compression can be accomplished by rotation of the device. For instance, FIG. 19, showing a buckling crown 240a which includes helical members 244 extending from a ring 246 attached to the distal end 302 of the tool 300. Additional helical members 248 which form the outer flange of the implant are connected to the helical members 244 by shearable connections 250. During deployment of the outer flange, the tool 300 is rotated while preventing the implant 204 from rotating with the result that the helical members 244 and 248 bend outwardly at the location of the shearable connections 250 and form the outer flange. After formation of the outer flange, the shearable connections 250 fracture releasing the implant 204 from the crown 240a which remains attached to the tool. As with the previously described device, the crown 240a can be attached to the tool in any desired manner, e.g. welding, molding, etc.

Figure 20:
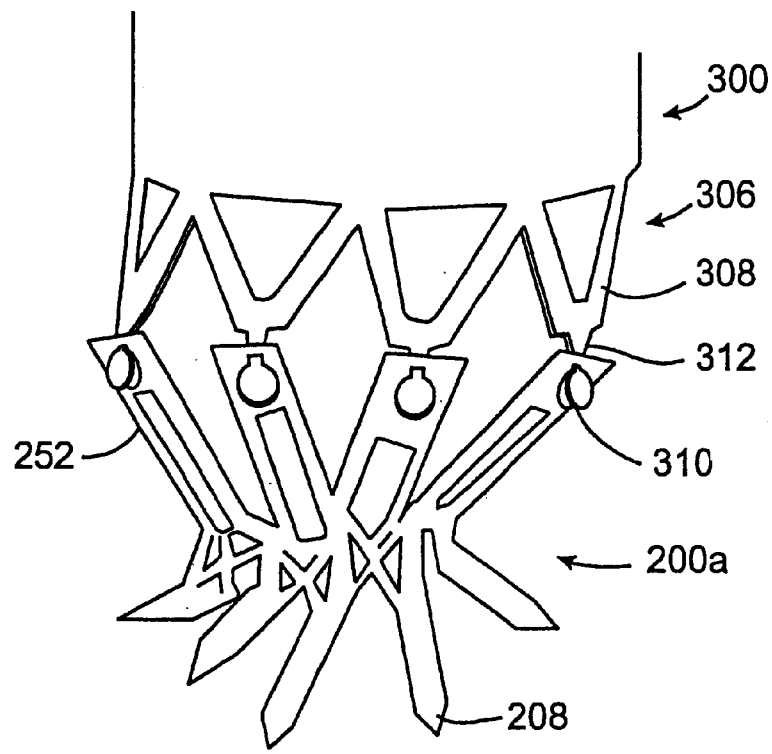
FIG. 20 shows a deforming crown design wherein the outer flange is formed from members which are mechanically attached to the tool.
Figure 21:
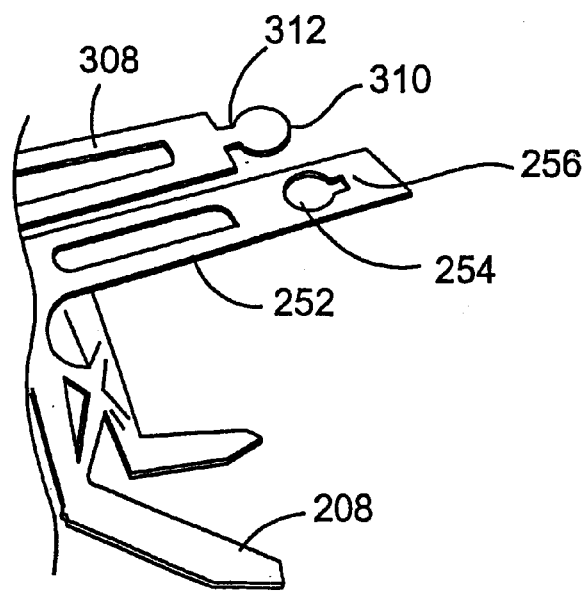
FIG. 21 shows how the members forming the outer flange are released from the deforming crown during formation of the outer flange.

According to the next embodiment, the device can be designed so as to be released from the tool without use of fracture elements. For example, the tool can include a deforming crown which mechanically disengages with the device after forming the outer flange. The device and tool can incorporate any suitable release mechanism which, for example, connects the crown to the deployment tool when a tensile force is applied to the connection but which disconnects when a compressive force is applied to the connection, e.g., hooks, tabs, spring clips, etc. FIG. 20 shows an embodiment of a tool with a deforming crown 306 comprised of struts 308 and tabs 310 connected to the struts 308 by thin necks 312. The device 200a is similar to device 200 except that device 200a does not include frangible links. Instead, device 200a includes bendable members 252 which are bent outwardly by the deforming crown 306 to form the outer flange. As shown in FIG. 21, each of the members 252 includes a hole 254 sized larger than the tabs to allow the tabs to be released from the holes after the outer flange is formed. When the device 200a is attached to the tool 300, the tabs 310 are fitted in the holes with the necks 312 received in the slots 256. The struts 308 can be shorter than the members 252 so that when the outer flange is formed the members 252 extend outwardly further than the struts 308. As a result, the necks 312 slide out of the slots 256 and the tabs 310 slide out of the holes 254 as the outer flange is formed and the implant is released from the tool.

Figure 22:
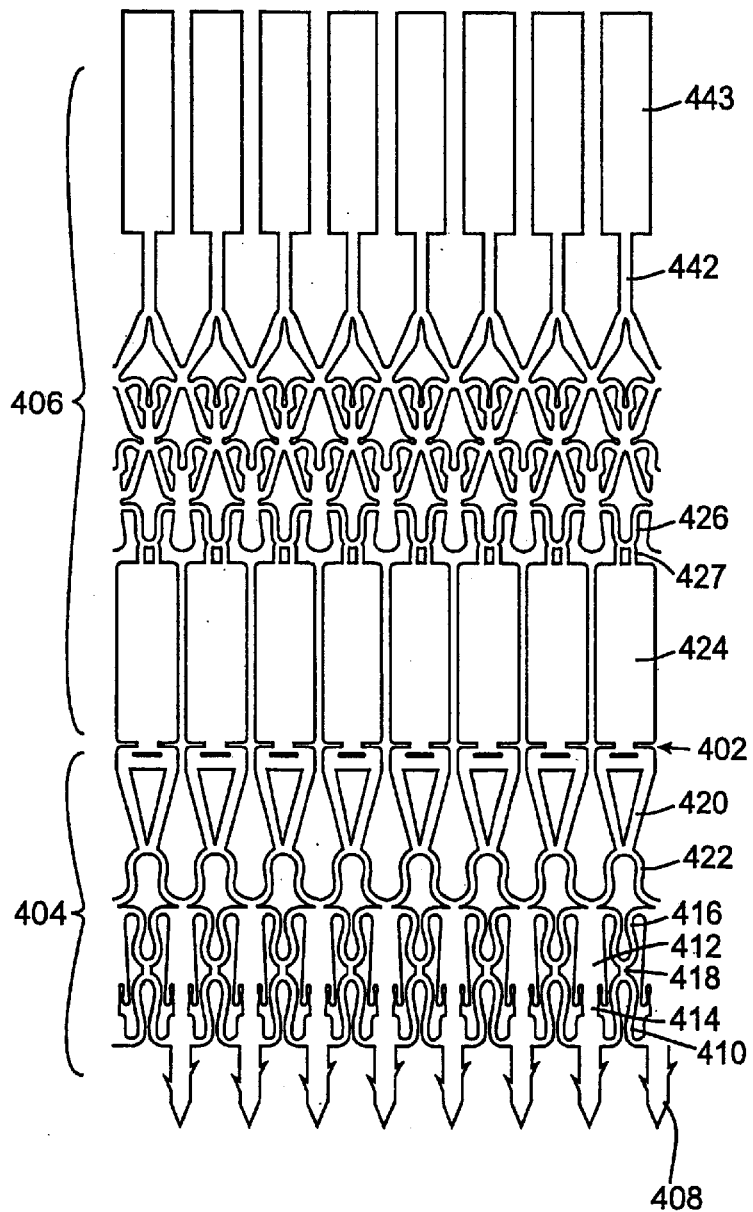
FIG. 22 shows (in planar form) a variation of the frangible anastomosis device shown in FIG. 13.

FIG. 22 shows a device 400 (illustrated in planar form for ease of description but which would be used in a tubular shape) which cooperates with a deployment tool (as described earlier) for delivering and deploying an implant 404 at a site in a living body. The device includes a frangible linkage 402 connecting the implant 404 to a discard portion 406. As explained with reference to the embodiment shown in FIGS. 13–14, after the device is positioned at a desired location, the implant 404 can be expanded to deploy an inner flange and subsequently axially compressed to deploy an outer flange while severing the implant 404 from the discard portion 406. The deployment tool can then be withdrawn along with the discard portion 406 which remains attached to the distal end of the deployment tool.

During radial expansion of the device, axially extending barbs 408 are pivoted outwardly by struts 410 such that the outwardly extending barbs 408 and struts 410 form the inner flange. To facilitate bending of the barbs, the barbs 408 comprise points on the ends of axially extending members 412 which have narrow sections 414 located a desired distance from the free ends of the barbs 408. For instance, the narrow sections 414 can be located at axial positions along the device corresponding approximately to the axial midpoint of the struts 410 connecting adjacent members 412 when the device is in the pre-expanded condition.

To facilitate easier bending of the struts 410 during radial expansion of the device, the distal ends of the struts can be curved at their points of attachment to the members 412. Likewise, a curved bend can be provided at the intersection where the proximal ends of the struts are attached together. When the device is radially expanded, the members 412 move radially outward and circumferentially apart as the struts 410 move radially outward until a force on the barbs 408 by the struts 410 causes the struts to become bent at the narrow sections 414, after which the barbs extend outwardly to form the inner flange. In this deployed condition, the barbs 408 are locked into position by an X-shaped frame formed by struts 410 and additional struts 416. The struts 416 are similar in configuration to the struts 410 with respect to how they are shaped and attached to the members 412. Short axially extending members 418 connect the intersection of the struts 410 to the intersection of the struts 416.

The frangible section 402 is located at the proximal ends of axially extending members 420 which are connected to the members 412 by U-shaped links 422. The members 420 are arranged in pairs which are attached together at midpoints of links 422. During radial expansion of the device, the individual links 422 are plastically deformed from their U-shaped configuration to form segments of a circumferentially extending annular ring. As a result, the device becomes shorter in the axial direction as links 422 form the annular ring and the distal ends of the pairs of members 420 attached to an individual link 422 move radially outward but not apart in the circumferential direction. At the same time, the proximal ends of the members 420 move radially outward and circumferentially apart.

Figure 23:
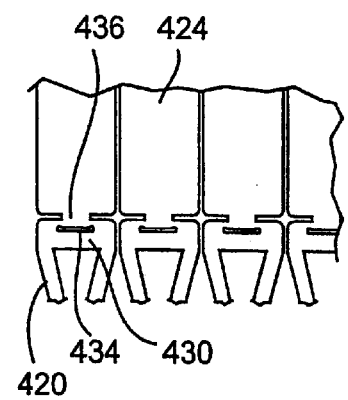
FIG. 23 shows details of a frangible link arrangement of the device shown in FIG. 22.

The frangible section 402 is located between axial members 420 and axially extending members 424. As shown in FIG. 22, the members 420 are closer together at their distal ends and this condition remains after expansion of the device. The proximal ends of the members 424 are attached to mid-points of U-shaped links 426 by a pair of short and closely spaced apart axially extending links 427. The distal ends of members 424 are connected to the proximal ends of the members 420 by a frangible joint comprised of shearable connections 402 which operate in a manner similar to the previously discussed connections 228, i.e., as shown in FIG. 23, the members 420 are connected at their proximal ends by a cross piece 430 and the members 424 include a projection 436 received in a recess 434. The frangible joint is formed from a unitary piece of material such as a laser cut tube wherein the shearable connections 402 comprise thin sections of material extending between opposite sides of the projection 436 and opposing walls of the recess 434. When the members 420 and 424 are pivoted to a sufficient extent, the shearable connections 402 are fractured allowing the implant to separate from the discard portion of the device.

The device 400 can be deployed in the same manner that the device 200 is deployed using deployment tool 300. That is, the device 400 includes a crown attached to a distal end of the deployment tool. The crown includes axially extending members 442 with tabs 443 on the proximal ends thereof, the members 442 being held in slots 304 of the tool 300 by the tabs 443. A plastic sleeve (not shown) can be placed over the slots 304 to prevent the members 442 from coming out of the slots. When mounted on the deployment tool, the crown is flared outwardly such that the members 442 are fully radially expanded at their proximal ends. During radial expansion of the device 400, the diamond shaped linkage of the crown 440 is expanded from an unexpanded condition like the configuration shown in FIG. 13 to an expanded condition like the expanded configuration shown in FIG. 14.

Figure 24:
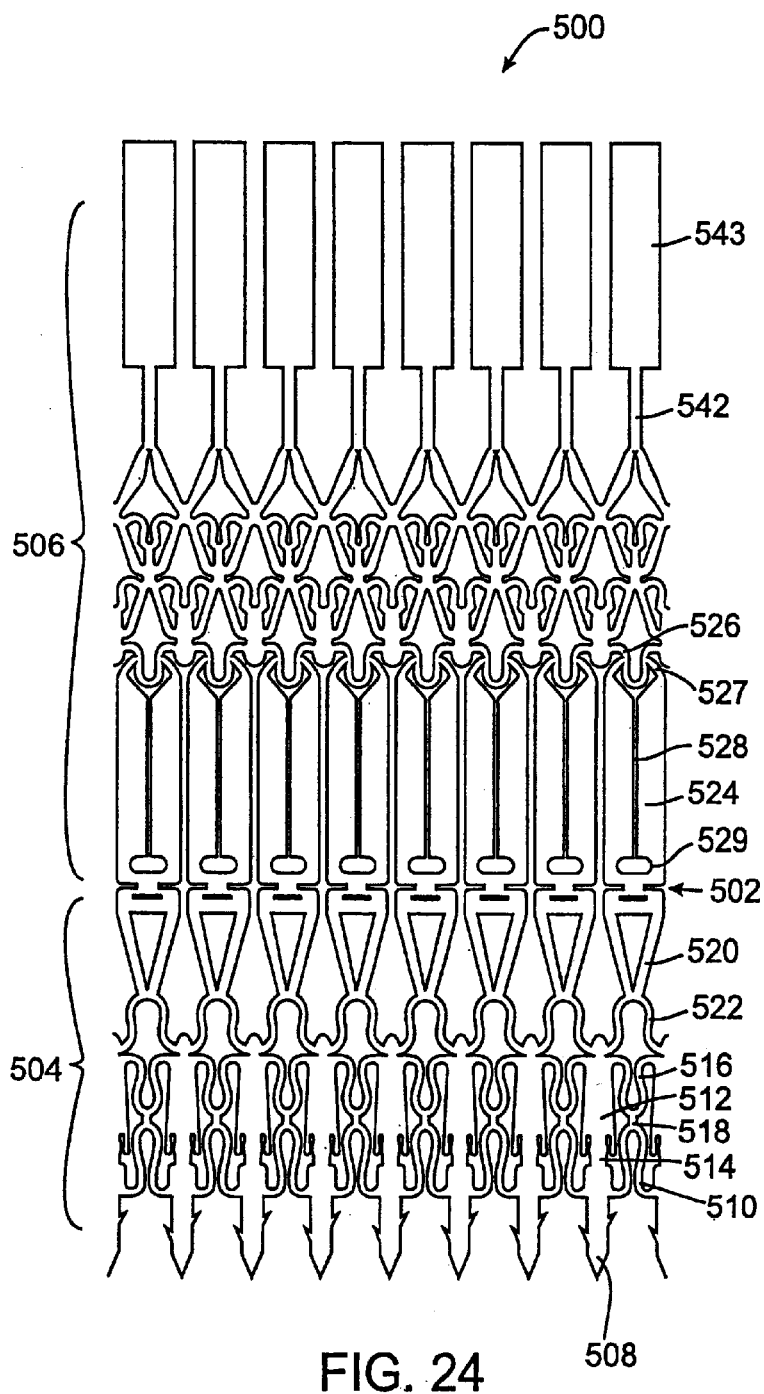
FIG. 24 shows (in planar form) a variation of the frangible anastomosis device shown in FIG. 13.

FIG. 24 shows a device 500 (illustrated in planar form for ease of description but which would be used in a tubular shape) which cooperates with a deployment tool (as described earlier) for delivering and deploying an implant 504 at a site in a living body. The device includes a frangible linkage 502 connecting the implant 504 to a discard portion 506. As explained with reference to the embodiment shown in FIGS. 13–14, after the device is positioned at a desired location, the implant 504 can be expanded to deploy an inner flange and subsequently axially compressed to deploy an outer flange while severing the implant 504 from the discard portion 506. The deployment tool can then be withdrawn along with the discard portion 506 which remains attached to the distal end of the deployment tool.

During radial expansion of the device, axially extending barbs 508 are pivoted outwardly by struts 510 such that the outwardly extending barbs 508 and struts 510 form the inner flange. To facilitate bending of the barbs, the barbs 508 comprise points on the ends of axially extending members 512 which have narrow sections 514 located a desired distance from the free ends of the barbs 508. For instance, the narrow sections 514 can be located at axial positions along the device corresponding approximately to the axial midpoint of the struts 510 connecting adjacent members 512 when the device is in the pre-expanded condition.

To facilitate easier bending of the struts 510 during radial expansion of the device, the distal ends of the struts can be curved at their points of attachment to the members 512. Likewise, a curved bend can be provided at the intersection where the proximal ends of the struts are attached together. When the device is radially expanded, the members 512 move radially outward and circumferentially apart as the struts 510 move radially outward until a force on the barbs 508 by the struts 510 causes the struts to become bent at the narrow sections 514, after which the barbs extend outwardly to form the inner flange. In this deployed condition, the barbs 508 are locked into position by an X-shaped frame formed by struts 510 and additional struts 516. The struts 516 are similar in configuration to the struts 510 with respect to how they are shaped and attached to the members 512. Short axially extending members 518 connect the intersection of the struts 510 to the intersection of the struts 516.

The frangible section 502 is located at the proximal ends of axially extending members 520 which are connected to the members 512 by U-shaped links 522. The members 520 are arranged in pairs which are attached together at only their distal ends. In particular, the distal ends of the links 522 are attached to proximal ends of the members 512 and the midpoint of each link 522 is attached to the distal ends of a respective pair of members 520. During radial expansion of the device, the individual links 522 are plastically deformed from their U-shaped configuration to form segments of a circumferentially extending annular ring. As a result, the device becomes shorter in the axial direction as links 522 form the annular ring and the distal ends of the members 520 move radially outward but not apart in the circumferential direction. At the same time, the proximal ends of the members 520 move radially outward and circumferentially apart.

Figure 25:
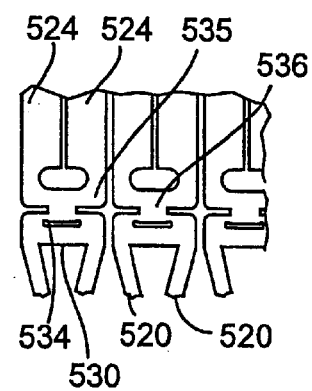
FIG. 25 shows details of a frangible link arrangement of the device shown in FIG. 24.

The frangible section 502 is located between pairs of the axial members 520 and pairs of axially extending members 524. As shown in FIG. 24, each pair of members 520 attached to an individual link 522 are closer together at their distal ends and this condition remains when the device is expanded. The proximal ends of pairs of the members 524 are attached at locations intermediate mid-points and ends of U-shaped links 526 by a pair of curved links 527. During expansion of the device, the U-shaped links 526 deform into a circumferentially extending ring and cause the proximal ends of the members 524 to spread apart such that a gap 528 between the members 524 becomes wider at the proximal ends of the members 524. To aid spreading of the members 524, the members include a curved recess 529 at the distal ends thereof. The distal ends of members 524 are connected to the proximal ends of the members 520 by a frangible joint comprised of shearable connections 502 which operate in a manner similar to the previously discussed connections 228, i.e., as shown in FIG. 25, the members 520 are connected at their proximal ends by a cross piece 530 and the members 524 are connected by a cross piece 535 which includes a projection 536 received in a recess 534. The frangible joint is formed from a unitary piece of material such as a laser cut tube wherein the shearable connections 502 comprise thin sections of material extending between opposite sides of the projection 536 and opposing walls of the recess 534. When the members 520 and 524 are pivoted to a sufficient extent, the shearable connections 502 are fractured allowing the implant to separate from the discard portion of the device.

The device 500 can be deployed in the same manner that the device 200 is deployed using deployment tool 300. That is, the device 500 includes a crown attached to a distal end of the deployment tool. The crown includes axially extending members 542 with tabs 543 on the proximal ends thereof, the members 542 being held in slots 304 of the tool 300 by the tabs 543. A plastic sleeve (not shown) can be placed over the slots 304 to prevent the members 542 from coming out of the slots. When mounted on the deployment tool, the crown is flared outwardly such that the members 542 are fully radially expanded at their proximal ends. During radial expansion of the device 500, the diamond shaped linkage of the crown 540 is expanded from an unexpanded condition like the configuration shown in FIG. 13 to an expanded condition like the expanded configuration shown in FIG. 14.

Figure 26:
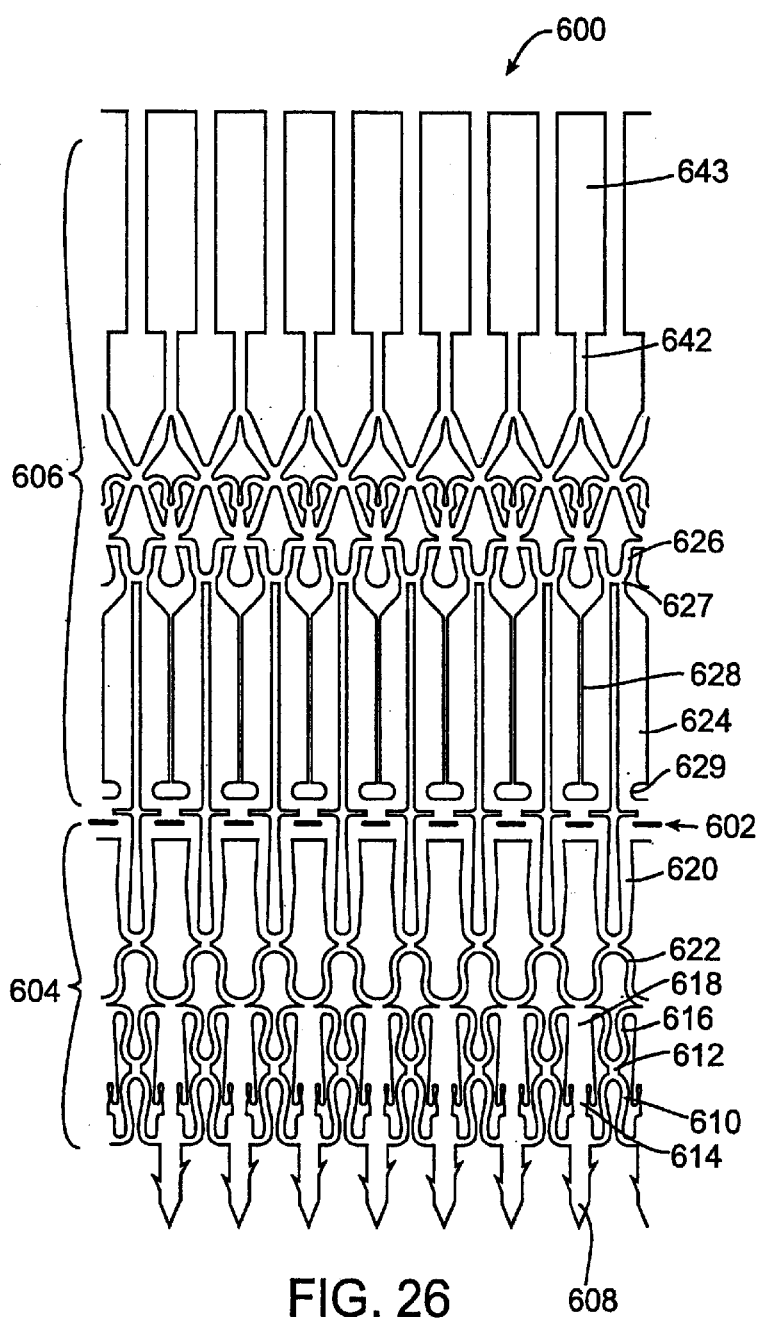
FIG. 26 shows (in planar form) a variation of the frangible anastomosis device shown in FIG. 13.

FIG. 26 shows a device 600 (illustrated in planar form for ease of description but which would be used in a tubular shape) which cooperates with a deployment tool (as described earlier) for delivering and deploying an implant 604 at a site in a living body. The device includes a frangible linkage 602 connecting the implant 604 to a discard portion 606. As explained with reference to the embodiment shown in FIGS. 13–14, after the device is positioned at a desired location, the implant 604 can be expanded to deploy an inner flange and subsequently axially compressed to deploy an outer flange while severing the implant 604 from the discard portion 606. The deployment tool can then be withdrawn along with the discard portion 606 which remains attached to the distal end of the deployment tool.

During radial expansion of the device, axially extending barbs 608 are pivoted outwardly by struts 610 such that the outwardly extending barbs 608 and struts 610 form the inner flange. To facilitate bending of the barbs, the barbs 608 comprise points on the ends of axially extending members 612 which have narrow sections 614 located a desired distance from the free ends of the barbs 608. For instance, the narrow sections 614 can be located at axial positions along the device corresponding approximately to a position slightly distal of the axial midpoint of the struts 610 connecting adjacent members 612 when the device is in the pre-expanded condition.

To facilitate easier bending of the struts 610 during radial expansion of the device, the distal ends of the struts can be curved at their points of attachment to the members 612. Likewise, a curved bend can be provided at the intersection where the proximal ends of the struts are attached together. When the device is radially expanded, the members 612 move radially outward and circumferentially apart as the struts 610 move radially outward until a force on the barbs 608 by the struts 610 causes the struts to become bent at the narrow sections 614, after which the barbs extend outwardly to form the inner flange. In this deployed condition, the barbs 608 are locked into position by an X-shaped frame formed by struts 610 and additional struts 616. The struts 616 are similar in configuration to the struts 610 with respect to how they are shaped and attached to the members 612. Short axially extending members 618 connect the intersection of the struts 610 to the intersection of the struts 616.

The frangible section 602 is located at the proximal ends of axially extending members 620 which are connected to the members 612 by U-shaped links 622. The members 620 are arranged as circumferentially spaced apart pairs which are attached together at midpoints of links 622. During radial expansion of the device, the individual links 622 are plastically deformed from their U-shaped configuration to form segments of a circumferentially extending annular ring. As a result, the device becomes shorter in the axial direction as links 622 form the annular ring. At the same time, the proximal ends of each pair of members 620 attached to an individual link 622 move radially outward and apart in the circumferential direction.

Figure 27:
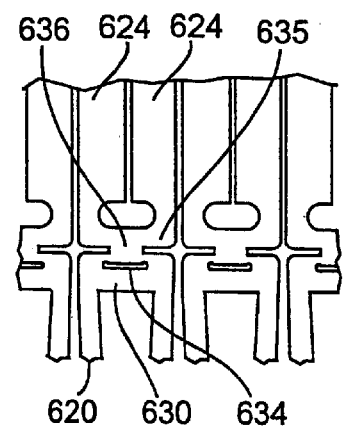
FIG. 27 shows details of a frangible link arrangement of the device shown in FIG. 26.

The frangible section 602 is located between pairs of the axial members 620 and pairs of axially extending members 624. As shown in FIG. 26, the members 620 are substantially parallel to each other when the device is in its unexpanded condition, i.e., prior to formation of the inner flange. However, when the device is radially expanded the distal ends of the members 620 will remain closer together than their proximal ends since the distal ends are attached to a midpoint of the links 622. The proximal ends of pairs of the members 624 are attached at mid-points of U-shaped links 626 by a pair of thin links 627. During expansion of the device, the U-shaped links 626 deform into a circumferentially extending ring while proximal ends of pairs of the members 624 spread apart such that a gap 628 between the pairs of members 624 becomes wider at the proximal ends of the members 624. To aid spreading of the pairs of members 624, the members 624 include a curved recess 629 at the distal ends thereof. The distal ends of members 624 are connected to the proximal ends of the members 620 by a frangible joint comprised of shearable connections 602 which operate in a manner similar to the previously discussed connections 228, i.e., as shown in FIG. 27, the members 620 are connected at their proximal ends by a cross piece 630 and the members 624 are connected by a cross piece 635 which includes a projection 636 received in a recess 634. The frangible joint is formed from a unitary piece of material such as a laser cut tube wherein the shearable connections 602 comprise thin sections of material extending between opposite sides of the projection 636 and opposing walls of the recess 634. When the members 620 and 624 are pivoted to a sufficient extent, the shearable connections 602 are fractured allowing the implant to separate from the discard portion of the device.

The device 600 can be deployed in the same manner that the device 200 is deployed using deployment tool 300. That is, the device 600 includes a crown attached to a distal end of the deployment tool. The crown includes axially extending members 642 with tabs 643 on the proximal ends thereof, the members 642 being held in slots 304 of the tool 300 by the tabs 643. A plastic sleeve (not shown) can be placed over the slots 304 to prevent the members 642 from coming out of the slots. When mounted on the deployment tool, the crown is flared outwardly such that the members 642 are fully radially expanded at their proximal ends. During radial expansion of the device 600, the diamond shaped linkage of the crown 640 is expanded from an unexpanded condition like the configuration shown in FIG. 13 to an expanded condition like the expanded configuration shown in FIG. 14.

FIG. 24 shows a device 700 (illustrated in planar form for ease of description but which would be used in a tubular shape) which cooperates with a deployment tool (as described earlier) for delivering and deploying an implant 704 at a site in a living body. The device includes a frangible linkage 702 connecting the implant 704 to a discard portion 706. As explained with reference to the embodiment shown in FIGS. 13–14, after the device is positioned at a desired location, the implant 704 can be expanded to deploy an inner flange and subsequently axially compressed to deploy an outer flange while severing the implant 704 from the discard portion 706. The deployment tool can then be withdrawn along with the discard portion 706 which remains attached to the distal end of the deployment tool.

During radial expansion of the device, axially extending barbs 708 are pivoted outwardly by struts 710 such that the outwardly extending barbs 708 and struts 710 form the inner flange. To facilitate bending of the barbs, the barbs 708 comprise points on the ends of axially extending members 712 which have narrow sections 714 located a desired distance from the free ends of the barbs 708. For instance, the narrow sections 714 can be located at axial positions along the device corresponding approximately to the axial midpoint of the struts 710 connecting adjacent members 712 when the device is in the pre-expanded condition.

To facilitate easier bending of the struts 710 during radial expansion of the device, the distal ends of the struts can be curved at their points of attachment to the members 712. Likewise, a curved bend can be provided at the intersection where the proximal ends of the struts are attached together. When the device is radially expanded, the members 712 move radially outward and circumferentially apart as the struts 710 move radially outward until a force on the barbs 708 by the struts 710 causes the struts to become bent at the narrow sections 714, after which the barbs extend outwardly to form the inner flange. In this deployed condition, the barbs 708 are locked into position by an X-shaped frame formed by struts 710 and additional struts 716. The struts 716 are similar in configuration to the struts 710 with respect to how they are shaped and attached to the members 712. Short axially extending members 718 connect the intersection of the struts 710 to the intersection of the struts 716.

The frangible section 702 is located at the proximal ends of axially extending members 720 which are connected to the members 712 by U-shaped links 722 and U-shaped links 723. The members 720 are arranged in pairs which are attached at their distal ends to proximal ends of the links 723 and the midpoints of the links 723 are attached to midpoints of the links 722. The ends of the links 722 are attached to the proximal ends of adjacent members 718. During radial expansion of the device, the individual links 722, 723 are plastically deformed from their U-shaped configuration to form segments of two circumferentially extending annular rings. As a result, the device becomes shorter in the axial direction as links 722, 723 form the annular rings and the distal ends of each pair of the members 720 attached to an individual link 723 move radially outward but not apart in the circumferential direction. At the same time, the proximal ends of pairs of the members 720 move radially outward and circumferentially apart.

Figures 28, 29:
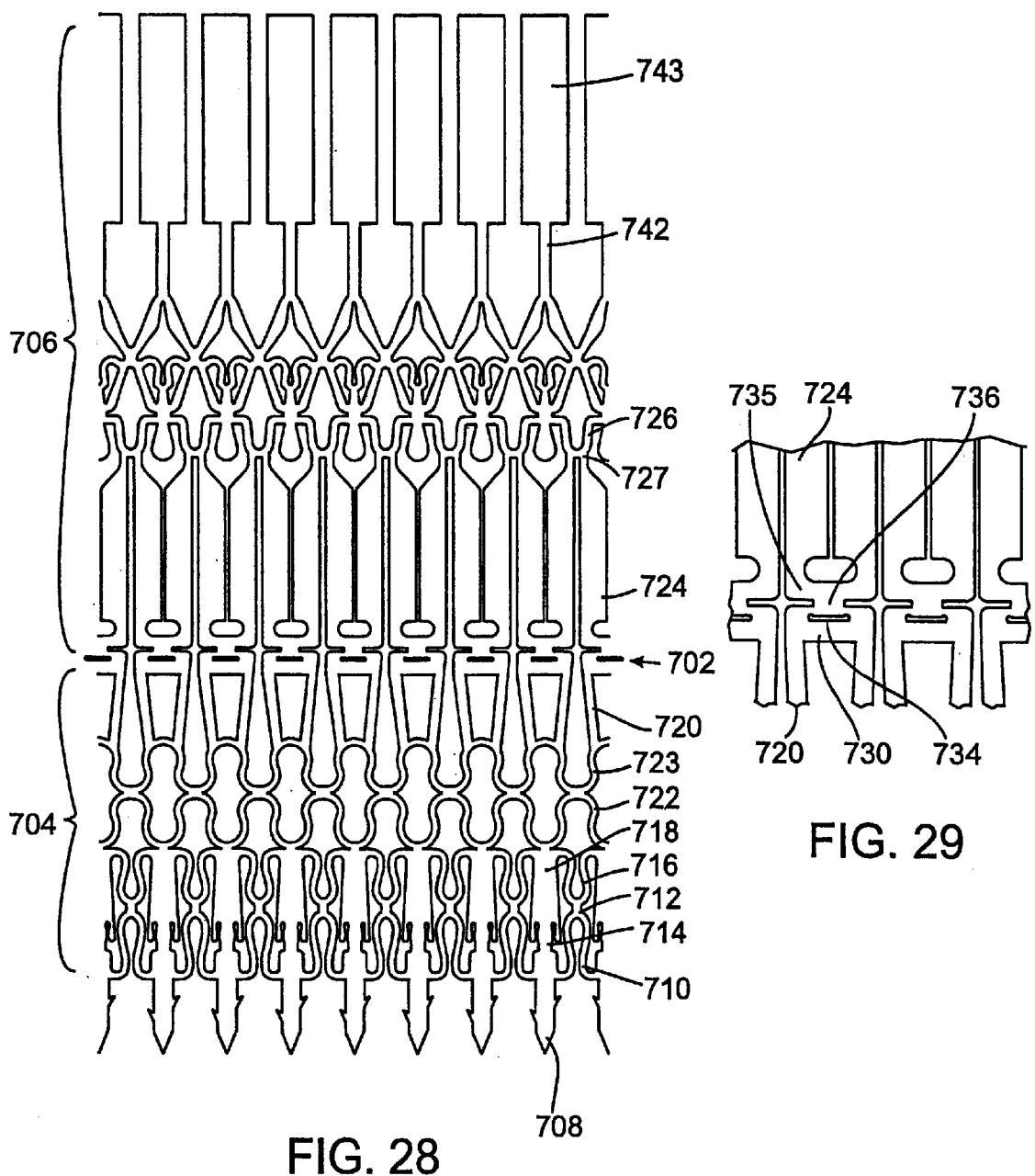
FIG. 28 shows (in planar form) a variation of the frangible anastomosis device shown in FIG. 13.
FIG. 29 shows details of a frangible link arrangement of the device shown in FIG. 28.

The frangible section 702 is located between pairs of the axial members 720 and pairs of axially extending members 724. As shown in FIG. 28, the members 720 attached to an individual link 722 are somewhat closer together at their distal ends than their proximal ends, a condition which remains after expansion of the device. The proximal ends of pairs of the members 724 are attached to mid-points of U-shaped links 726 by a pair of short links 727. During expansion of the device, the U-shaped links 726 deform into a circumferentially extending ring and cause the proximal ends of the members 724 to spread apart such that a gap 728 between the members 724 becomes wider at the proximal ends of the members 724. To aid spreading of the members 724, the members include a curved recess 729 at the distal ends thereof. The distal ends of members 724 are connected to the proximal ends of the members 720 by a frangible joint comprised of shearable connections 702 which operate in a manner similar to the previously discussed connections 228, i.e., as shown in FIG. 29, the members 720 are connected at their proximal ends by a cross piece 730 and the members 724 are connected by a cross piece 735 which includes a projection 736 received in a recess 734. The frangible joint is formed from a unitary piece of material such as a laser cut tube wherein the shearable connections 702 comprise thin sections of material extending between opposite sides of the projection 736 and opposing walls of the recess 734. When the members 720 and 724 are pivoted to a sufficient extent, the shearable connections 702 are fractured allowing the implant to separate from the discard portion of the device.

The device 700 can be deployed in the same manner that the device 200 is deployed using deployment tool 300. That is, the device 700 includes a crown attached to a distal end of the deployment tool. The crown includes axially extending members 742 with tabs 743 on the proximal ends thereof, the members 742 being held in slots 304 of the tool 300 by the tabs 743. A plastic sleeve (not shown) can be placed over the slots 304 to prevent the members 742 from coming out of the slots. When mounted on the deployment tool, the crown is flared outwardly such that the members 742 are fully radially expanded at their proximal ends. During radial expansion of the device 700, the diamond shaped linkage of the crown 740 is expanded from an unexpanded condition like the configuration shown in FIG. 13 to an expanded condition like the expanded configuration shown in FIG. 14.

Figure 30:
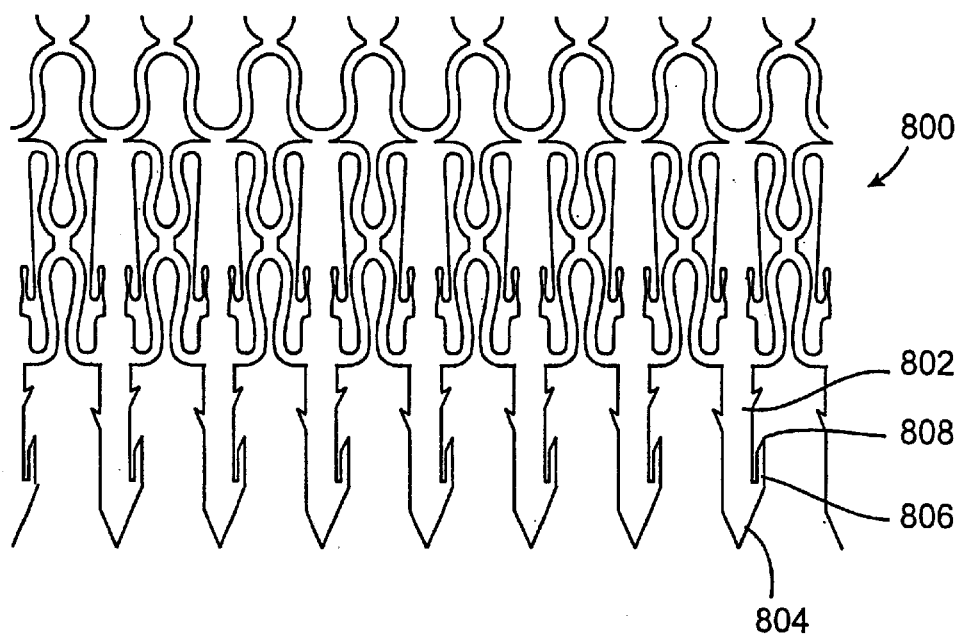
FIGS. 30 and 31 show details of a tissue anchoring arrangement.
Figure 31:
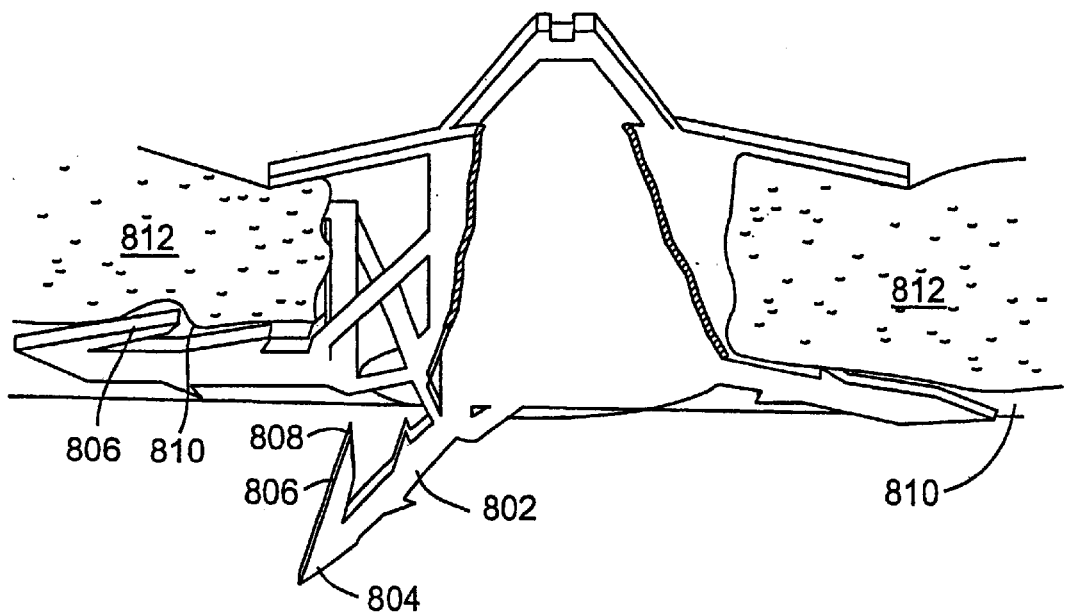

FIGS. 30 and 31 show details of a tissue anchoring arrangement which can optionally be incorporated in the anastomosis device according to the invention. In particular, FIG. 30 shows a distal end of a device 800 (illustrated in planar form for ease of description but which would be used in a tubular shape) wherein axially extending members 802 having points 804 for penetrating the graft vessel (as described earlier) also include a tissue anchoring arrangement 806. The tissue anchoring arrangement 806 comprises one or more projections (e.g., tangs or barbs) extending from one or both sides of the members 802, the projections providing anchor points against the inner surface 810 of the target vessel 812, as shown in FIG. 31 (wherein illustration of the graft vessel has been omitted). The projections 806 can include points 808 which embed themselves in the tissue of the target vessel with or without penetrating the tissue. It is desirable that the projections provide enough of an anchoring effect to prevent sudden increases in blood pressure in the target vessel (after the anastomosis operation) from rupturing the seal between the graft vessel and the target vessel created by the anastomosis device. The outer flange can also include anchoring projections which can be used in lieu of or addition to anchoring projections on the inner flange.

Figure 32:
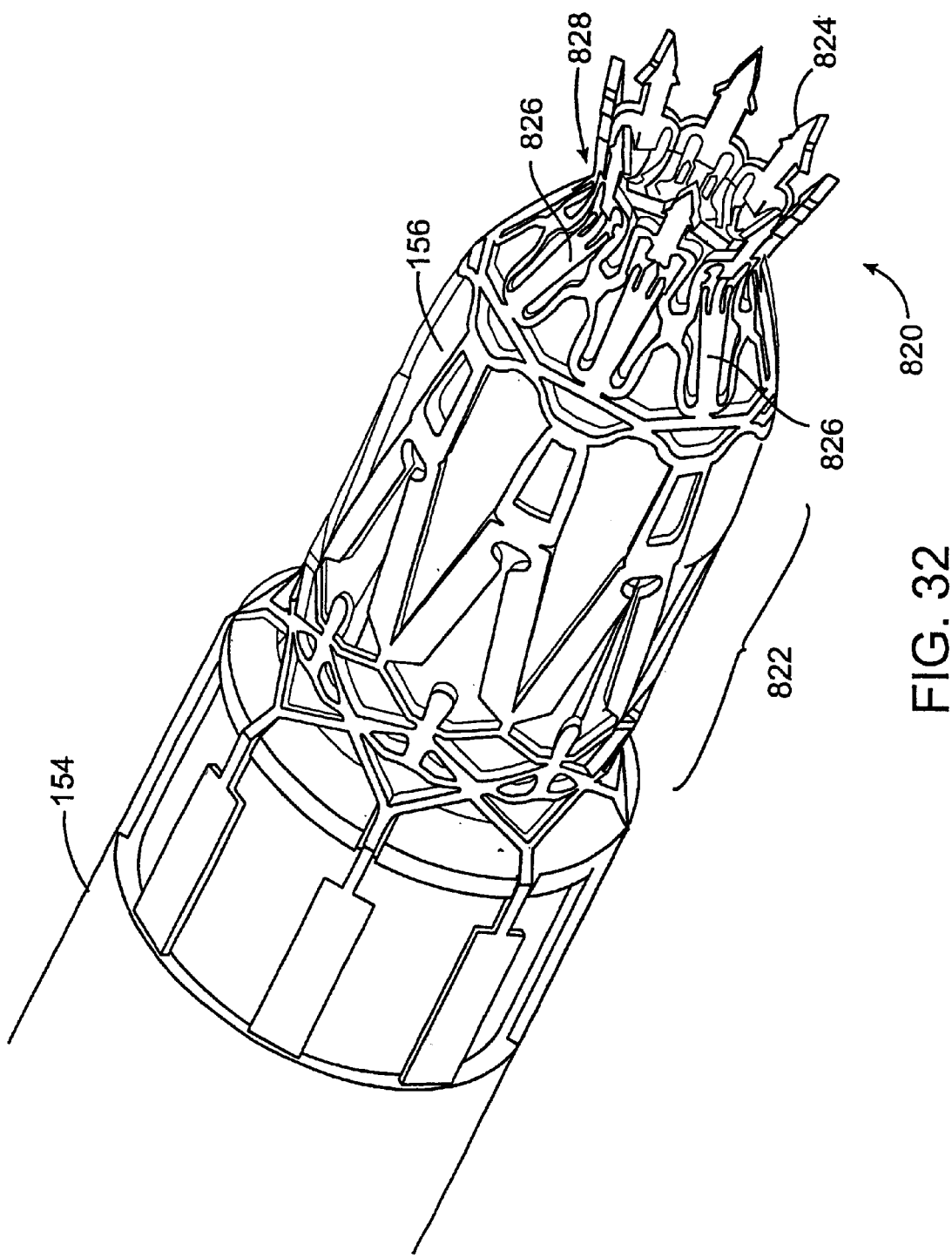
FIG. 32 shows details of how an anastomotic device in accordance with the invention can be deployed.

A preferred method of loading an expander 156 in a holder tube 154 and placing a graft vessel over the anastomosis device is explained with reference to FIG. 32, wherein expander 156 has been inserted in holder tube 154. However, prior to insertion of the expander, the barbed ends 824 of device 820 preferably are bent outwardly so as to form an angle such as 5 to 60° to the central axis of the device. Afterwards, the expander 156 can be advanced within the holder tube 154 to a location at which a proximal portion 822 of anastomosis device 820 is expanded over the expander. As a result of contact of the beveled end of the expander 156 with axial members 826, the barbed ends 824 can be rotated inwardly somewhat to form a smaller angle with the central axis of the device 820. Then, after a graft vessel is threaded through the anastomosis device 820, the end of the graft vessel can be everted over the distal end of the anastomosis device and the barbed ends 824 can be poked through the graft vessel. Details of how this eversion process can be carried out are set forth in commonly assigned U.S. patent application Ser. No. 09/440,166 filed on Nov. 15, 1999. With the anastomosis device and everted graft vessel in such a condition, the holder tube 154 can be loaded in a trocar (not shown). Details of preferred trocar designs and an explanation of how the trocar creates an incision in a target vessel can be found in commonly assigned U.S. patent application Ser. No. 09/440,263 (filed Nov. 15, 1999).

In order to deploy the device 820, the inner flange can be expanded by pushing the expander 156 a set distance while maintaining the holder tube 154 in a fixed position. As a result, the linkage of the inner flange rotates the barbed ends 824 about the hinged connections 828 such that the barbed ends 824 from an angle of 40 to 140° with the central axis. Then, the holder tube 154 is pushed a set distance while holding the expander 156 in a fixed position to deploy the outer flange. As a result, the linkage of the outer flange and the discard portion of the anastomosis device is axially compressed such that the linkage fractures as the outer flange is rotated outwardly and towards the already deployed inner flange.

Figure 33:
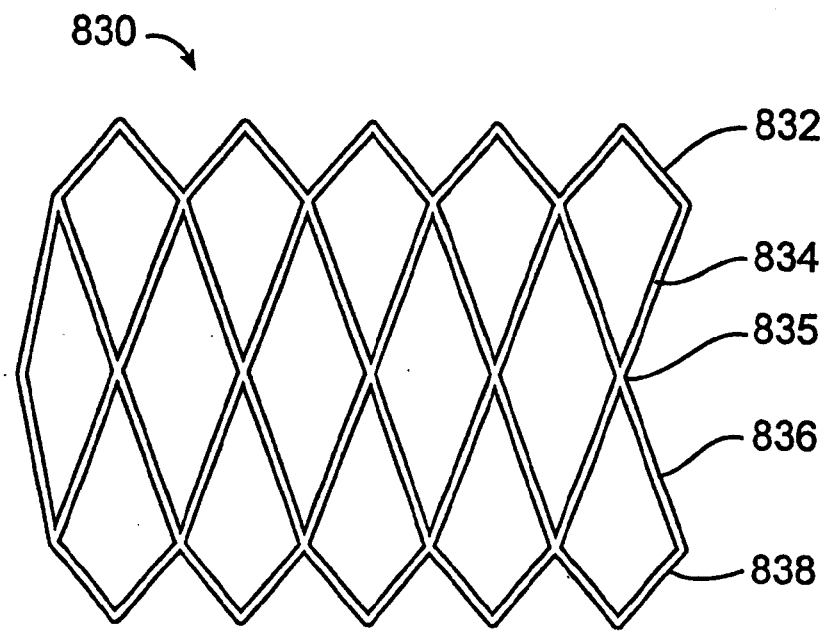
FIGS. 33 and 34 show a further embodiment of the anastomotic device.
Figure 34:
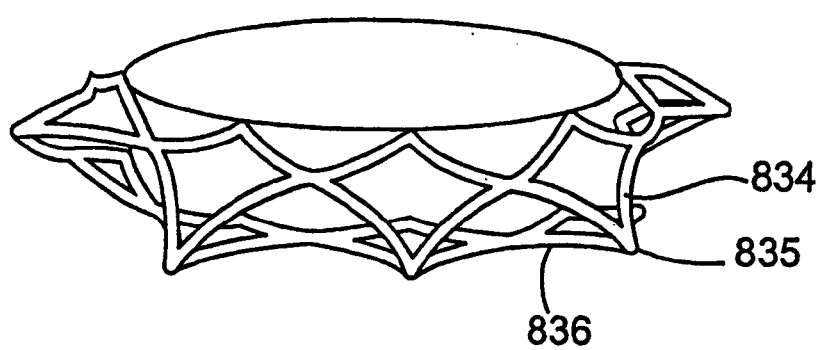

Each of the anastomosis devices described above are preferably single piece devices which are formed by laser cutting or punching from a tube or sheet of material. The devices may be provided in varying sizes to join vessels such as arteries, veins, bile ducts, etc., of different sizes. Although various linkage arrangements have been shown wherein the devices include struts which extend between two circumferentially spaced apart locations and axial members which extend between two axially spaced apart locations, the linkages which form the flanges could also be formed by V-shaped links arranged in diamond like patterns. For example, FIG. 33 shows an example of a tubular mesh 830 which can be axially compressed to form an outwardly extending flange. The mesh 830 includes short links 832 and 838 and long links 834 and 836, the links 832 and 834 being joined to form a first diamond shaped pattern, the links 834 and 836 being joined to form a second diamond shaped pattern, and the links 836 and 838 being joined to form a third diamond shaped pattern. With such an arrangement, axial compression of the tubular mesh 830 will cause the links 834 and 836 to pivot about joints 835 connecting the links 834 to the links 836 and thus form a flange as illustrated in FIG. 34.

The mesh 830 can be joined to another mesh with the same or different linkage arrangement with or without a connecting linkage therebetween. If the same linkage arrangement is used, in order to obtain deployment of one flange prior to deployment of the other flange, one of the linkages can be made with wider and/or thicker links. For example, by using a distal linkage of thin links and a proximal linkage of thick links, it is possible to deploy the inner flange prior to deployment of the outer flange. In other words, axial compression of the tubular mesh can cause the weaker distal linkage to deploy first and form the inner flange after which the outer flange can be formed by axial compression of the stronger proximal linkage.

Although the invention has been principally discussed with respect to coronary bypass surgery, the anastomosis devices of the present invention may be used in other types of anastomosis procedures. For example, the anastomosis device may be used in femoral—femoral bypass, vascular shunts, subclavian-carotid bypass, organ transplants, and the like.

The anastomosis devices may be made of any known material which can be bent and will retain the bent shape such as stainless steel, nickel titanium alloys, and the like. The hinges or pivot joints which have been discussed above in the various embodiments of the present invention may be designed to concentrate the bending at a desired location.

While the invention has been described in detail with reference to the preferred embodiments thereof, it will be apparent to one skilled in the art that various changes and modifications can be made and equivalents employed, without departing from the present invention.

What is claimed is:

1. An anastomosis device that cooperates with a deployment tool for connecting an end of a graft vessel to a target vessel, the anastomosis device comprising:
   a deployable section including a first linkage deformable by the deployment tool to form at least one flange and a second linkage connected to said first linkage;
   a discard section; and
   frangible links that connect said second linkage to said discard section and cooperate with the deployment tool to form at least one flange in said deployable section.

2. The anastomosis device of claim 1, wherein said first flange presses a portion of the graft vessel into contact with an inner surface of the target vessel and said second flange presses another portion of the graft vessel into contact with an outer surface of the target vessel.

3. The anastomosis device of claim 1, wherein a connecting portion extends between the first and second linkages; and wherein said first linkage and said second linkage each comprise a plurality of axial members, each of said axial members comprising a weakened area that allows said axial member to bend outwardly.

4. The anastomosis device of claim 1, wherein at least one of said piercing members comprises an anchor projection configured to hold said first flange against an inner wall of the target vessel.

5. The anastomosis device of claim 1, wherein said first linkage is radially expandable, and wherein said first linkage includes a plurality of links arranged in a configuration such that an axial dimension of said first linkage changes upon radial expansion of said first linkage.

6. The anastomosis device of claim 5, wherein said second linkage comprises a plurality of axial members, wherein neighboring ones of said axial members are closer together at distal ends thereof than at proximal ends thereof after said second flange is formed.

7. The anastomosis device of claim 1, wherein said first and second flanges each form an angle with an axis of the device between substantially 40 and substantially 140 degrees.

8. The anastomosis device of claim 1, wherein said first linkage comprises axial members that move radially outward and circumferentially apart when said first flange is formed.

9. The anastomosis device of claim 1, wherein the anastomosis device is radially expandable along at least a portion of its length, and wherein said first linkage comprises axial members and struts, said struts connected to and forming an X-shaped pattern between neighboring axial members, said struts causing said axial members to bend at pivot points and form said first flange during radial expansion of the anastomosis device.

10. The anastomosis device of claim 1, wherein prior to formation of said first flange, said second linkage comprises axial members and U-shaped links, each U-shaped link connected substantially at its midpoint to an end of at least one said axial members, and wherein said U-shaped links are formed into annular rings during formation of said first flange.

11. The anastomosis device of claim 1, wherein said second linkage comprises at least one anchor projection configured to hold said second flange against an outer wall of the target vessel.

12. The anastomosis device of claim 1, wherein said deployable section comprises:
    a first linkage deformable by the deployment tool to form a first flange; and
    a second linkage connected to said first linkage, wherein said second linkage is deformable by the deployment tool to form a second flange that together with said first flange connects the graft vessel to the target vessel.

13. The anastomosis device of claim 12, further comprising at least one piercing member extending from at least one said linkage.

14. The anastomosis device of claim 13, wherein at least one of said piercing members extends at least partially in the distal direction.

15. The anastomosis device of claim 12, wherein said second linkage comprises a plurality of second linkage members and said discard section comprises a plurality of discard section members; wherein at least one set of two adjacent second linkage members are connected by a first crosspiece and a recess is defined adjacent said first crosspiece; wherein at least one set of two adjacent discard section members are connected by a second crosspiece, further comprising a projection extending from said second crosspiece, wherein each said frangible link connects a corresponding said recess and said projection.

16. The anastomosis device of claim 15, wherein said projection comprises a plurality of elements.

17. The anastomosis device of claim 12, wherein said second linkage comprises a plurality of second linkage members and said discard section comprises a plurality of discard section members; wherein at least one set of two adjacent second linkage members are connected by a first crosspiece and at least one set of two adjacent discard section members are connected by a second crosspiece; wherein at least two first projections extend from said first crosspiece and at least two second projections extend from said second crosspiece; wherein said first projections and said second projections are interleaved; and wherein at least one said first projection is connected to at least one adjacent said second projection by a frangible link.

18. The anastomosis device of claim 1, wherein at least one said frangible link is a shearable connection.

19. An anastomosis device deployment system for deploying the anastomosis device of claim 1, comprising:
    a handle;
    a holder attached to said handle, said holder having a distal end configured to hold the anastomosis device with an attached graft vessel; and
    an expander positioned within said holder and slidable with respect to said holder to a position at which the expander is positioned within the anastomosis device and radially expands the anastomosis device.

20. The system of claim 19, further comprising a trocar moveable relative to said holder to form an opening in a target vessel to receive the anastomosis device and the attached graft vessel.

21. The system of claim 20, wherein said trocar is a split trocar slidable over said holder and the anastomosis device.

22. The system of claim 19, wherein said holder is substantially tubular.

23. The system of claim 19, wherein said holder and said expander are configured to be positioned outside a lumen of the target vessel.

24. An anastomosis system for connecting an end of a graft vessel to a target vessel, comprising:

a deployment tool; and an anastomosis device, wherein said deployment tool is slidable relative to said anastomosis device, the anastomosis device comprising:
- a first linkage, wherein said deployment tool applies a force to said first linkage to form a first flange; and
- a second linkage, wherein said deployment tool applies a force to said second linkage to form a second flange that together with said first flange connects the graft vessel to the target vessel.

25. The system of claim 24, wherein said deployment tool is configured to be positioned outside the lumen of the target vessel.

26. The anastomosis device of claim 24, wherein said first flange presses a portion of the graft vessel into contact with an inner surface of the target vessel and said second flange presses another portion of the graft vessel into contact with an outer surface of the target vessel.

27. The anastomosis device of claim 24, wherein said first linkage includes a plurality of links arranged in a configuration such that an axial dimension of said first linkage changes upon radial expansion of the first linkage.

28. An anastomosis device for connecting an end of a graft vessel to a target vessel, comprising:

a first linkage having at least one piercing member extending therefrom at least partially in the distal direction; and a second linkage connected to said first linkage, said second linkage proximal to said first linkage.

* * * * *